(12) United States Patent
Kosuge et al.

(10) Patent No.: US 8,110,294 B2
(45) Date of Patent: Feb. 7, 2012

(54) MATERIAL FOR ORGANIC LIGHT-EMITTING ELEMENT AND ORGANIC LIGHT-EMITTING ELEMENT INCLUDING THE SAME

(75) Inventors: Tetsuya Kosuge, Kawasaki (JP); Jun Kamatani, Tokyo (JP); Naoki Yamada, Inagi (JP); Ryota Ooishi, Yokohama (JP); Shinjiro Okada, Kamakura (JP)

(73) Assignee: Canon Kabushiki Kaisha, Tokyo (JP)

( * ) Notice: Subject to any disclaimer, the term of this patent is extended or adjusted under 35 U.S.C. 154(b) by 617 days.

(21) Appl. No.: 12/031,341

(22) Filed: Feb. 14, 2008

(65) Prior Publication Data
US 2008/0200736 A1 Aug. 21, 2008

(30) Foreign Application Priority Data

Feb. 20, 2007 (JP) ................................. 2007-039334

(51) Int. Cl.
*H01L 51/54* (2006.01)
*C07C 15/00* (2006.01)
*H01J 1/63* (2006.01)

(52) U.S. Cl. .......... 428/690; 428/917; 585/26; 313/504; 313/506

(58) Field of Classification Search ........................ None
See application file for complete search history.

(56) References Cited

U.S. PATENT DOCUMENTS

| | | | |
|---|---|---|---|
| 7,229,702 B2 | 6/2007 | Saitoh et al. | 428/690 |
| 7,241,513 B2 | 7/2007 | Suzuki et al. | 428/690 |
| 7,687,154 B2 * | 3/2010 | Iwawaki et al. | 428/690 |
| 7,691,492 B2 * | 4/2010 | Yamada et al. | 428/690 |
| 2005/0123793 A1 * | 6/2005 | Thompson et al. | 428/690 |
| 2005/0158580 A1 * | 7/2005 | Ito et al. | 428/690 |
| 2005/0236977 A1 | 10/2005 | Yamada et al. | 313/504 |
| 2005/0244670 A1 | 11/2005 | Saitoh et al. | 428/690 |
| 2005/0276994 A1 | 12/2005 | Iwawaki et al. | 428/690 |
| 2006/0003171 A1 | 1/2006 | Igawa et al. | 428/447 |
| 2006/0066225 A1 | 3/2006 | Kishino et al. | 313/504 |

(Continued)

FOREIGN PATENT DOCUMENTS

JP 11-144875 5/1999

(Continued)

OTHER PUBLICATIONS

Chemistry—A European Journal (2001), 13(5), pp. 1423-1431.*

(Continued)

*Primary Examiner* — Dawn L. Garrett
(74) *Attorney, Agent, or Firm* — Fitzpatrick, Cella, Harper & Scinto

(57) ABSTRACT

A fluorene compound and an organic light-emitting element including the fluorene compound are provided. The fluorene compound is represented by the following general formula [1], and the fluorene compound is a material for an organic light-emitting element. A steric hindrance group is introduced directly on a fluorene ring in the fluorene compound.

[1]

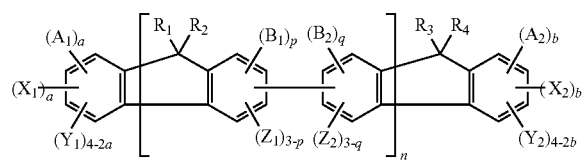

14 Claims, 2 Drawing Sheets

U.S. PATENT DOCUMENTS

| | | | |
|---|---|---|---|
| 2006/0113528 A1 | 6/2006 | Okinaka et al. | 257/40 |
| 2006/0121312 A1* | 6/2006 | Yamada et al. | 428/690 |
| 2006/0141287 A1* | 6/2006 | Klubek et al. | 428/690 |
| 2006/0166034 A1 | 7/2006 | Saitoh et al. | 428/690 |
| 2007/0122652 A1 | 5/2007 | Hashimoto et al. | 428/690 |
| 2007/0184302 A1 | 8/2007 | Iwawaki et al. | 428/690 |
| 2007/0285010 A1* | 12/2007 | Lee et al. | 313/504 |

FOREIGN PATENT DOCUMENTS

| | | |
|---|---|---|
| JP | 11-162642 | 6/1999 |
| JP | 2004-043349 | 2/2004 |
| JP | 2004-277368 | 10/2004 |
| JP | 2004-277377 | 10/2004 |

OTHER PUBLICATIONS

Organic Letters, (2006), 8(7), pp. 1499-1502.*

Proceedings for SPIE—The International Society for Optical Eng. (2004), 5519, (Organic Light emitting Materials and Devices VIII), pp. 24-34.*

Beaupré et al., "Optical and Electrical Properties of π-Conjugated Polymers Based on Electron-Rich 3,6-Dimethoxy-9,9-dihexylfluorene Unit," *Macromolecules*, vol. 36, No. 24, 8986-8991 (2003).

Yang et al., "Theoretical Investigation of Optical and Electronic Property Modulations of π-Conjugated Polymers Based on the Electron-Rich 3,6-Dimethoxy-fluorene Unit," *J. Org. Chem.*, vol. 70, No. 8, 3009-3020 (2005).

Hartwig et al., "Room-Temperature Palladium-Catalyzed Amination of Aryl Bromides and Chlorides and Extended Scope of Aromatic C-N Bond Formation with a Commercial Ligand," *J. Org. Chem.*, vol. 64, No. 15, 5575-5580 (1999).

* cited by examiner

MATERIAL FOR ORGANIC LIGHT-EMITTING ELEMENT AND ORGANIC LIGHT-EMITTING ELEMENT INCLUDING THE SAME

BACKGROUND OF THE INVENTION

1. Field of the Invention

The present invention relates to a fluorene compound for an organic light-emitting element and an organic light-emitting element using the fluorene compound.

2. Description of the Related Art

In the organic light-emitting element, a thin film containing a fluorescent organic compound or a phosphorescent organic compound is held between an anode and a cathode, and electrons and holes are injected from the respective electrodes. Consequently, excitons of the fluorescent organic compound or the phosphorescent organic compound are generated, and the light emitted when the exciton returns to a ground state is used in the element.

Recently, the organic light-emitting elements have developed significantly. Since desired features now include light-emitting devices having a high luminance at a low applied voltage, a diversity of wavelengths of emitted light, high-speed performance, low profile, and light weight, the possibilities of wide-ranging applications have been explored.

However, these possibilities require an output of light having a higher luminance or a higher conversion efficiency. Furthermore, emission of blue, green, and red light with higher color purity is required for full color displays or the like. These issues have not yet been solved satisfactorily.

Much research has been conducted on aromatic compounds and fused polycyclic aromatic compounds serving as luminescent organic compounds for light-emitting layers or the like. However, one cannot say that a fully satisfactory compound has been obtained from the viewpoint of the luminance of emitted light and the like.

Documents related to the present invention include Japanese Unexamined Patent Application Publication Nos. 11-144875, 11-162642, 2004-43349, 2004-277368, and 2004-277377 as patent documents and Macromolecules, 36, 8986 (2003) and J. Org. Chem., 70, 3009 (2005) as non-patent documents. However, no disclosure has been made with respect to a fluorene compound, as disclosed in the present invention, serving as a material for an organic light-emitting element and having a high triplet excited state $T_1$ level based on the presence of a steric hindrance group on a fluorene ring. There is no example in which such a sterically hindered fluorene compound is applied to an organic light-emitting element.

SUMMARY OF THE INVENTION

The present invention has been made in order to solve the above-described problems. The present invention provides an organic light-emitting element having a high-efficiency, high-luminance output of light.

The present invention was made after intensive research in order to solve the above-described problems. Accordingly, the present invention provides a material for an organic light-emitting element and an organic light-emitting element using the material, as described below.

A material for an organic light-emitting element according to an aspect of the present invention (hereafter abbreviated as "according to the present invention") is the material represented by General formula [I]:

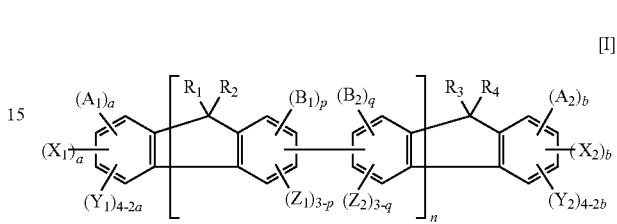

wherein in the formula, $R_1$ to $R_4$ represent independently a hydrogen atom or a substituted or unsubstituted alkyl group, $X_1$ and $X_2$ represent independently a substituted or unsubstituted heterocyclic group or a substituted amino group, $Y_1$ and $Y_2$ represent independently a group selected from the group consisting of a hydrogen atom, a substituted or unsubstituted alkyl group, a substituted or unsubstituted phenyl group, and a substituted or unsubstituted alkoxy group, $Z_1$ and $Z_2$ represent independently a group selected from the group consisting of a hydrogen atom, a substituted or unsubstituted alkyl group, and a substituted or unsubstituted alkoxy group, $A_1$, $A_2$, $B_1$, and $B_2$ represent independently a substituted or unsubstituted alkyl group or a substituted or unsubstituted alkoxy group, $A_1$ is a substituent at an ortho-position relative to the substituent $X_1$, $A_2$ is a substituent at an ortho-position relative to the substituent $X_2$, $B_1$ and $B_2$ are independently a substituent at an ortho-position relative to a fluorene-fluorene bond, n represents an integer of 0 to 4, a and b represent independently 0 or 1, the relationship, $n+a+b \geq 1$, is satisfied, p and q represent independently an integer of 0 to 2, the relationship, $p+q \geq 1$, is satisfied when $n \neq 0$, p groups of $B_1$ may be the same or different from each other, q groups of $B_2$ may be the same or different from each other, (4-2a) groups of $Y_1$ may be the same or different from each other, (4-2b) groups of $Y_2$ may be the same or different from each other, (3-p) groups of $Z_1$ may be the same or different from each other, (3-q) groups of $Z_2$ may be the same or different from each other, and types of fluorene may be the same or different from each other when n is 2 or more.

The above-described material for an organic light-emitting element can be preferably represented by General formula [II]:

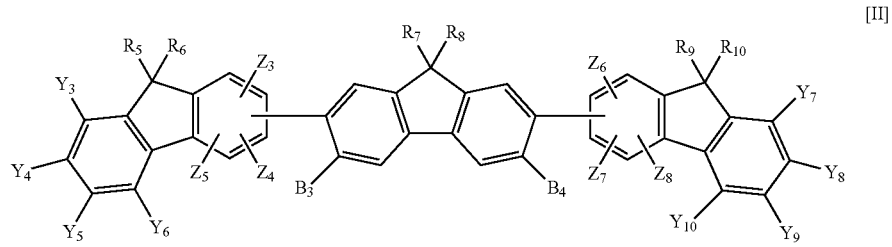

wherein in the formula, $R_5$ to $R_{10}$ represent independently a hydrogen atom or a substituted or unsubstituted alkyl group, $Y_3$ to $Y_{10}$ represent independently a group selected from the group consisting of a hydrogen atom, a substituted or unsubstituted alkyl group, a substituted or unsubstituted phenyl group, and a substituted or unsubstituted alkoxy group, $Z_3$ to $Z_8$ represent independently a group selected from the group consisting of a hydrogen atom, a substituted or unsubstituted alkyl group, and a substituted or unsubstituted alkoxy group, and $B_3$ and $B_4$ represent independently a substituted or unsubstituted alkyl group or a substituted or unsubstituted alkoxy group.

In another embodiment the above-described material for an organic light-emitting element can be represented by General formula [III]:

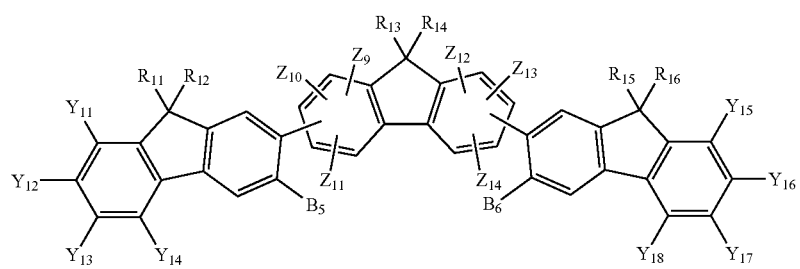

wherein in the formula, $R_{11}$ to $R_{16}$ represent independently a hydrogen atom or a substituted or unsubstituted alkyl group, $Y_{11}$ to $Y_{18}$ represent independently a group selected from the group consisting of a hydrogen atom, a substituted or unsubstituted alkyl group, a substituted or unsubstituted phenyl group, and a substituted or unsubstituted alkoxy group, $Z_9$ to $Z_{14}$ represent independently a group selected from the group consisting of a hydrogen atom, a substituted or unsubstituted alkyl group, and a substituted or unsubstituted alkoxy group, and $B_5$ and $B_6$ represent independently a substituted or unsubstituted alkyl group or a substituted or unsubstituted alkoxy group.

In a further embodiment the above-described material for an organic light-emitting element can be represented by General formula [IV]:

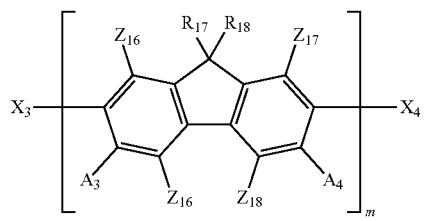

wherein in the formula, $R_{17}$ and $R_{18}$ represent independently a hydrogen atom or a substituted or unsubstituted alkyl group, $X_3$ and $X_4$ represent independently a substituted or unsubstituted heterocyclic group or a substituted amino group, $Z_{15}$ to $Z_{18}$ represent independently a group selected from the group consisting of a hydrogen atom, a substituted or unsubstituted alkyl group, and a substituted or unsubstituted alkoxy group, $A_3$ and $A_4$ represent independently a substituted or unsubstituted alkyl group or a substituted or unsubstituted alkoxy group, m represents an integer of 1 to 3, and the types of fluorene units may be the same or different from each other when m is 2 or more.

In yet another embodiment the above-described material for an organic light-emitting element can be represented by General formula [V]:

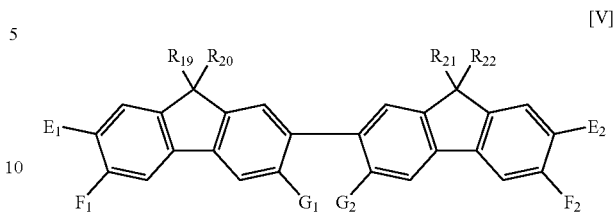

wherein in the formula, $R_{19}$ to $R_{22}$ represent independently a hydrogen atom or a substituted or unsubstituted alkyl group, $E_1$ and $E_2$ represent independently a group selected from the group consisting of a hydrogen atom, a substituted or unsubstituted phenyl group, a substituted or unsubstituted heterocyclic group, and a substituted amino group, $F_1$ and $F_2$ represent independently a group selected from the group consisting of a hydrogen atom, a substituted or unsubstituted alkyl group, and a substituted or unsubstituted alkoxy group, but do not represent independently a hydrogen atom when $B_1$ and $B_2$, which are substitutents at ortho-places relative to $F_1$ and $F_2$, respectively, are independently a substituted or unsubstituted heterocyclic group or a substituted amino group, and $G_1$ and $G_2$ represent independently a group selected from the group consisting of a hydrogen atom, a substituted or unsubstituted alkyl group, and a substituted or unsubstituted alkoxy group, but do not represent hydrogen atoms at the same time.

An organic light-emitting element according to the present invention can include at least one pair of electrodes composed of an anode and a cathode, at least one of which is transparent or translucent, and an organic compound layer held between the pair of electrodes, wherein the organic compound layer contains the above-described material for an organic light-emitting element.

In the above-described organic light-emitting element, the organic compound layer can be a light-emitting layer.

In the above-described organic light-emitting element, the light-emitting layer can include at least two compounds of a host compound and a guest compound, and the host compound can be the above-described material for an organic light-emitting element.

In the above-described organic light-emitting element, at least one type of the above-described guest compound can be a phosphorescent compound.

The above-described organic light-emitting element can be a field-emitting element for emitting light by applying a voltage between the above-described pair of electrodes.

The organic light-emitting element including the material for an organic light-emitting element according to the present invention, in particular, the phosphorescent element can have a high-efficiency, high-luminance output of light.

Further features of the present invention will become apparent from the following description of exemplary embodiments with reference to the attached drawings.

DESCRIPTION OF THE EMBODIMENTS

Figure 1:
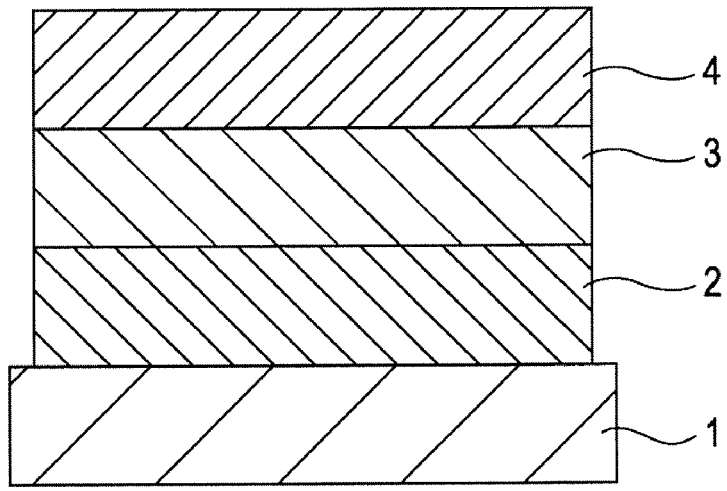
FIG. 1 is a sectional view showing an example of an organic light-emitting element according to the present invention.

The present invention will be described below in detail.

A fluorene compound, which is a material for an organic light-emitting element according to the present invention, will be described.

In general, in the case where a light-emitting layer of an organic light-emitting element includes a host compound and a guest compound, which have a carrier transport property, a primary process for emitting light is composed of the following several steps.

(1) Transportation of electrons and holes in the light-emitting layer
(2) Generation of an exciton of the host
(3) Excitation energy transmission between host compounds
(4) Excitation energy transfer from the host to the quest Desired energy transfer or light emission in each step occurs due to various deactivation processes and competition.

Of course an emission quantum yield of an emission center material itself is required to be significant in order to increase the luminous efficacy of the organic light-emitting element. In addition, there is an important consideration of how to conduct the energy transfer between the hosts or between the host and the guest, efficiently. Regarding the phosphorescent element, in order to obtain high-efficiency phosphorescence emission, it is also necessary to confine triplet excitons within the interior of the light-emitting layer and to effect radiative deactivation efficiently by preventing energy transfer of the triplet excitons to the hosts. Consequently, it is important that a compound is employed having large triplet energy at a triplet excited state $T_1$ level higher than the level of the light-emitting layer guest compound for the light-emitting layer host and that a charge transport layer is in contact with the light-emitting layer.

The present inventors have conducted various studies, and, as a result, it was found that organic light-emitting elements including the fluorene compounds, which are represented by General formulae [1] to [V] and which have high $T_1$ levels, exhibited high-luminous-efficiency, high-luminance emission of light.

In general, a fluorene ring and, in particular, an oligofluorene site, in which fluorene rings are joined to each other, exhibit good carrier conductivity. Therefore, compounds including them as partial structures in molecules are used as materials for organic light-emitting elements. The $T_1$ level of the fluorene molecule is 422 nm (2.94 eV), whereas the $T_1$ level of the oligofluorene compound, including the oligofluorene site, is low because oligofluorene has a planar structure in the triplet excited state $T_1$. Consequently, if the oligofluorene compound is used for an element to emit phosphorescence of colors with wavelengths corresponding to blue to green, the $T_1$ energy of the light-emitting material is transferred to the oligofluorene compound and, thereby, nonradiative deactivation occurs, so that it becomes difficult to obtain high-efficiency emission of light.

In order to solve the above-described problem, in the material for an organic light-emitting element according to the present invention, a sterically hindered substituent is introduced at an ortho-position relative to a fluorene-fluorene bond, and, accordingly, the fluorene-fluorene bond is twisted, so that conjugation is partly disturbed. Consequently, the fluorene compound according to the present invention has a $T_1$ level higher than that of a common oligofluorene compound. Therefore, even when the fluorene compound is used for an element to emit phosphorescence of colors with wavelengths smaller than the wavelength corresponding to red, high-efficiency emission of light can be obtained.

Other than the method of the present invention, a method in which fluorene rings are joined through a 2-methyl-p-phenylene group, a m-phenylene group, or the like is also known as a method for raising the $T_1$ level of the oligofluorene compound. However, because the fluorene compound according to the present invention has few rotation sites since the fluorene rings are joined directly to each other, it therefore, provides a structure more advantageous to carrier transfer, as compared with the structures of the above-noted fluorene-phenylene-fluorene compounds. Furthermore, the present invention provides enhanced results in an evaporation process as well. For example, in the case where a compound having a large number of total fluorene rings is used, a further undesired increase in molecular weight due to an unintended increase in the number of joining phenylene groups does not occur and film formation can be conducted by evaporation at relatively low temperatures.

Likewise, the above-described effect of raising the $T_1$ level is also exerted regarding a fluorene-heterocyclic ring bond and a fluorene-substituted amino bond. Therefore, in the case where compounds including them as partial structures are used for charge transport layers of phosphorescent elements, a positive effect is exerted on confinement of triplet excitons and high-efficiency emission of light can be obtained.

Furthermore, in the case where the fluorene compound includes both a heterocyclic ring and a substituted amino group in the molecule and has the above-described steric hindrance, then, when used as a bipolar phosphorescent layer host, the carrier balance in the light-emitting layer can be controlled and a phosphorescent element having not only high luminous efficacy, but also good driving durability, is obtained.

Moreover, the fluorene compound according to the present invention can be a low molecular weight compound represented by General formula [1] where n is 4 or less, and, more favorably, a fluorene compound having a molecular weight of 1,000 or less from the viewpoint of a method for refining a material and for film formation by evaporation.

The present invention has been made by using a fluorene compound whose molecule is designed on the basis of the above-described consideration.

Regarding the fluorene compound which is a material for an organic light-emitting element according to the present invention, examples of suitable alkyl groups include a methyl group, an ethyl group, a n-propyl group, a n-butyl group, a n-pentyl group, a n-hexyl group, a n-heptyl group, a n-octyl group, a n-decyl group, an iso-propyl group, an iso-propyl d7 group, an iso-butyl group, a sec-butyl group, a tert-butyl group, a tert-butyl-d9 group, an iso-pentyl group, a neopentyl group, a tert-octyl group, a cyclopropyl group, a cyclobutyl group, a cyclopentyl group, a cyclohexyl group, a norbornyl group, and an adamantyl group. Other alkyl groups can also be employed.

Examples of substituted or unsubstituted heterocyclic groups include a pyridyl group, a pyridadyl group, a pyrimidinyl group, a pyrazinyl group, a triazyl group, a quinolyl group, an isoquinolyl group, a phthalazinyl group, a quinazolinyl group, a quinoxalinyl group, a naphthyridinyl group, an acridinyl group, a phenanthrolyl group, a diazafluorenyl group, a phenazinyl group, a pyrrolyl group, a pyrazolyl group, an imidazolyl group, a triazolyl group, an indolyl group, an indolyzinyl group, a benzimidazolyl group, a carbazolyl group, a benzocarbazolyl group, a thienyl group, a benzothienyl group, a dibenzothienyl group, a furyl group, a benzofuryl group, an isobenzofuryl group, a dibenzofuryl group, an oxazolyl group, an isooxazolyl group, a benzoxazolyl group, an oxadiazolyl group, a thiazolyl group, an isothiazolyl group, a benzothiazolyl group, and a thiadiazolyl group, as well as other heterocycles.

Examples of substituted amino groups include a dimethylamino group, a diethylamino group, a dibenzylamino group, a diphenylamino group, a ditolylamino group, a dinaphthylamono group, a difluorenylamino group, a N-naphthyl-N'-phenylamino group, and a N-fluorenyl-N'-phenylamino group, as well as others.

Examples of alkoxy groups include a methoxy group, an ethoxy group, a propoxy group, a n-butoxy group, and a tert-butoxy group, for example.

Examples of groups which may become substituents of the above-described alkyl groups, heterocyclic groups, alkoxy groups, and phenyl groups include alkyl groups, e.g., a methyl group, an ethyl group, and a tert-butyl group; aromatic hydrocarbon groups, e.g., a phenyl group, a naphthyl group, a phenanthryl group, a fluorenyl group, a biphenylenyl group, and a triphenylenyl group; heterocyclic groups, e.g., a thienyl group, a pyrrolyl group, a pyridyl group, and a quinolyl group; substituted amino groups, e.g., a dimethylamino group, a diethylamino group, a dibenzylamino group, and a diphenylamino group; alkoxy groups, e.g., a methoxy group and an ethoxy group; halogen atoms, e.g., fluorine, chlorine, bromine, and iodine; a hydroxyl group; a cyano group; and a nitro group, and others.

Regarding the compounds according to the present invention, a hydrogen substituent may be replaced by deuterium.

In the fluorene compounds represented by General formulae [1] to [V] according to the present invention, the substituents $R_1$ to $R_{22}$ at position 9 of fluorene can be unsubstituted alkyl groups from the viewpoint of thermal stability and chemical stability. A methyl group and an ethyl group are more favorable.

In the fluorene compounds represented by General formulae [1] to [V] according to the present invention, the sterically hindered substituents $A_1$ to $A_4$, $B_1$ to $B_6$, $F_1$, $F_2$, $G_1$, and $G_2$ for raising the $T_1$ level can be unsubstituted alkyl groups from the viewpoint of thermal stability and chemical stability. A methyl group is particularly favorable because the methyl group reduces the conjugation appropriately so as to prevent the band gap from becoming excessively large.

Typical exemplary structural formulae of fluorene compounds containing sterically hindered groups according to the present invention will be described below.

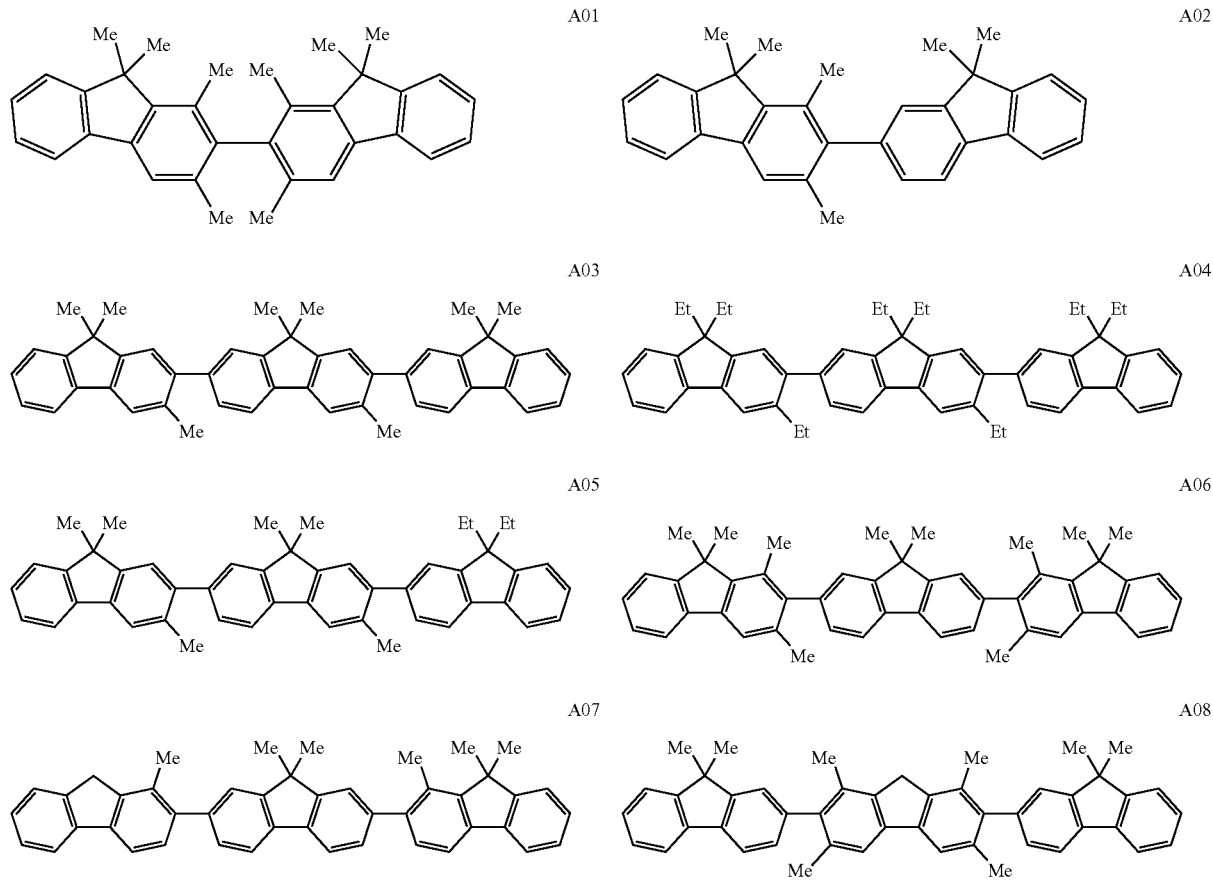

-continued
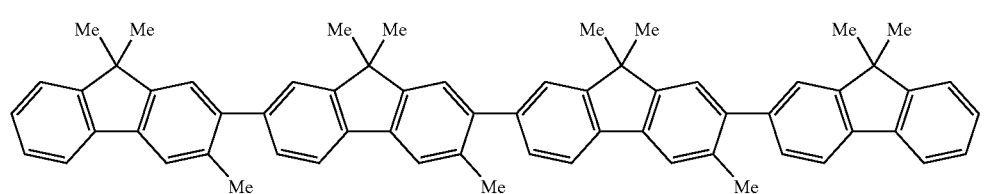
A09
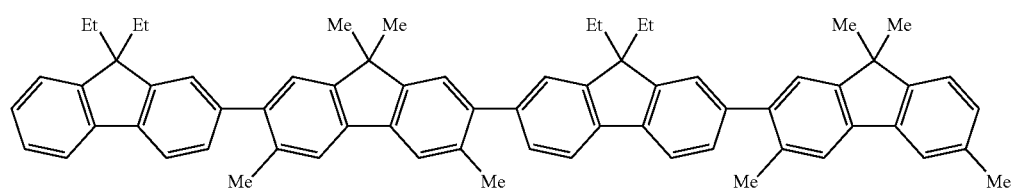
A10
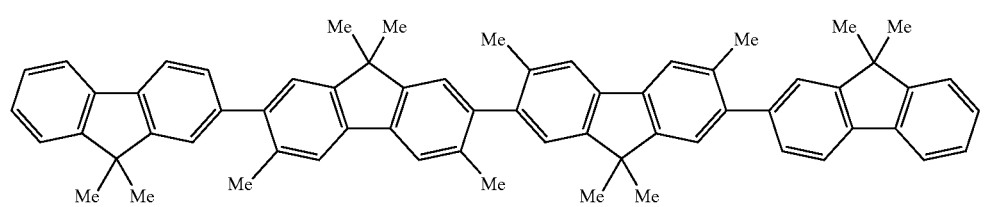
A11
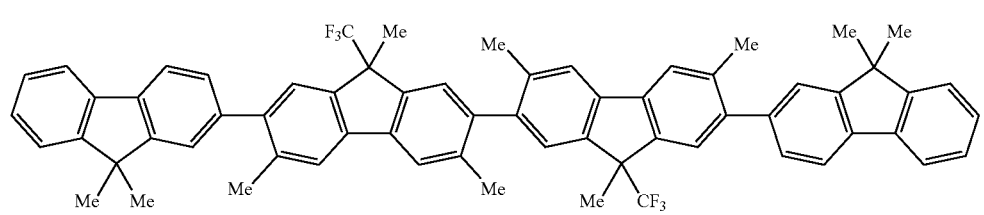
A12
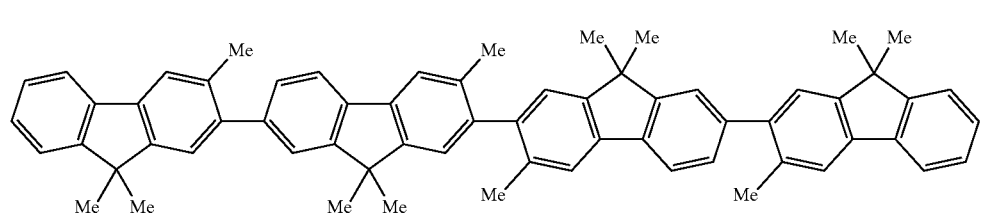
A13
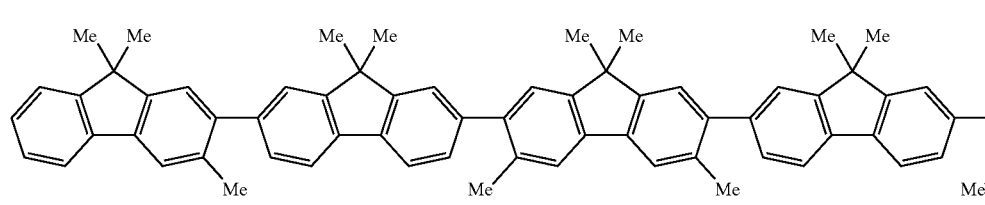
A14
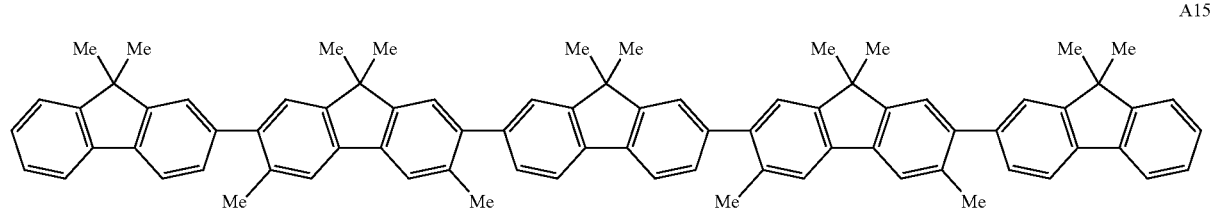
A15
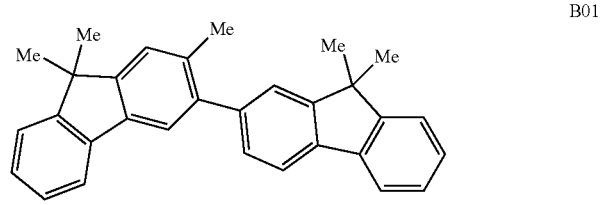
B01
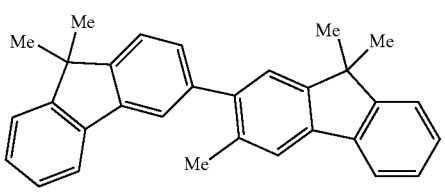
B02

-continued
B03
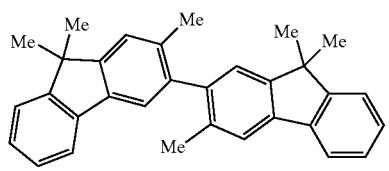
B04
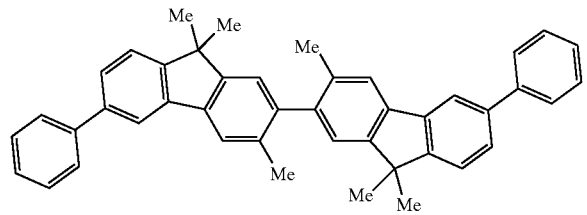
B05
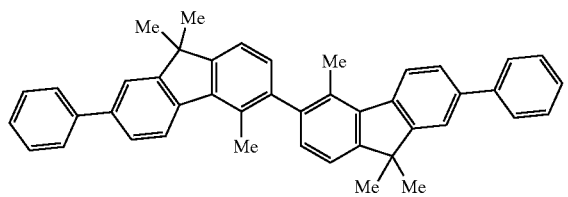
B06
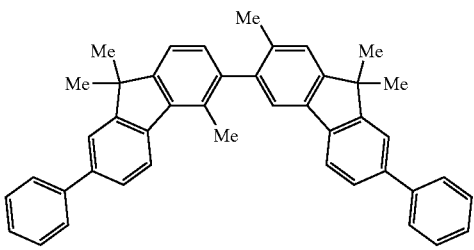
B07
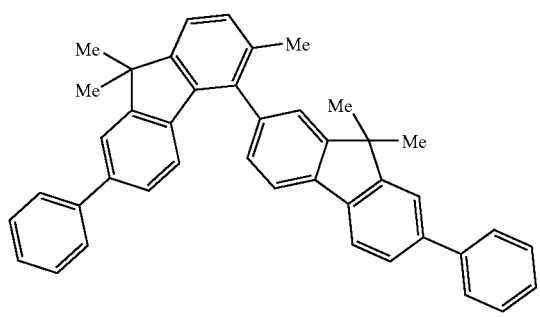
B08
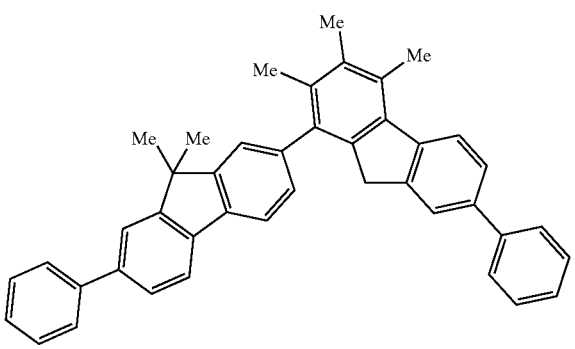
B09
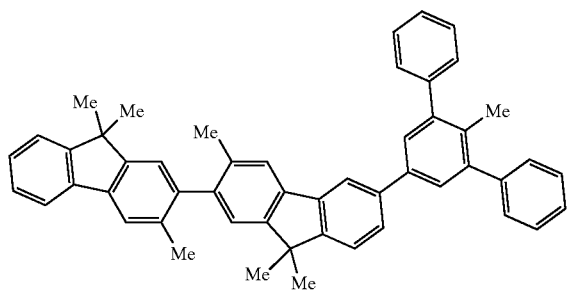
B10
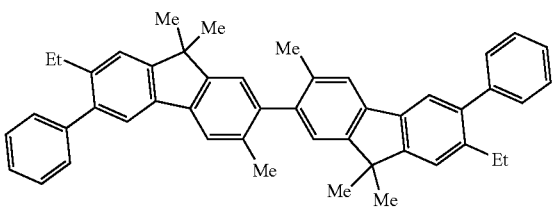
B11
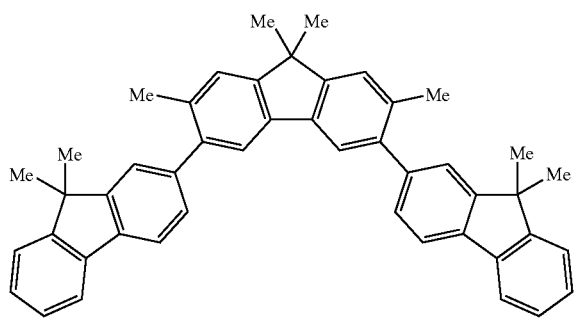
B12
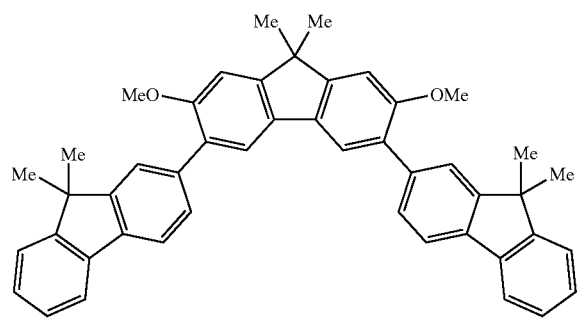

-continued
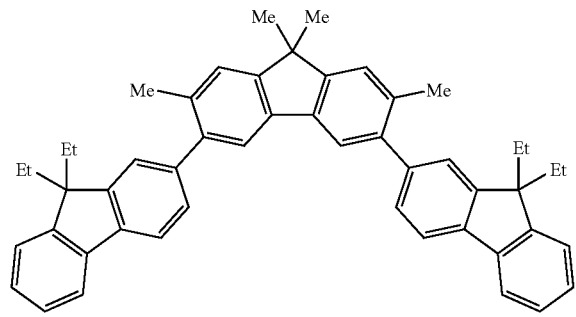
B13
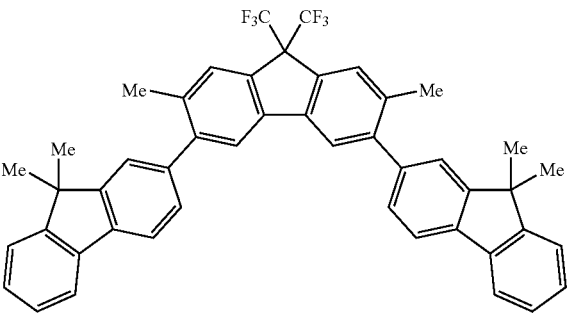
B14
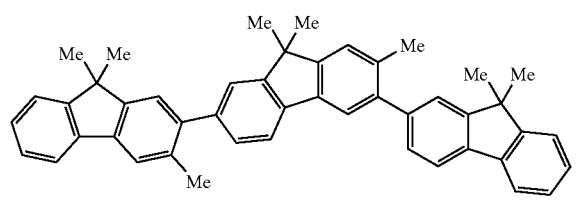
B15
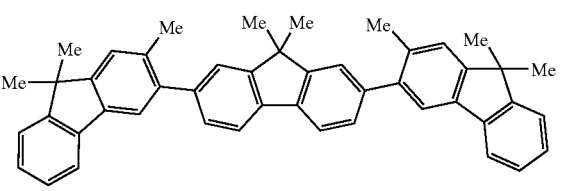
B16
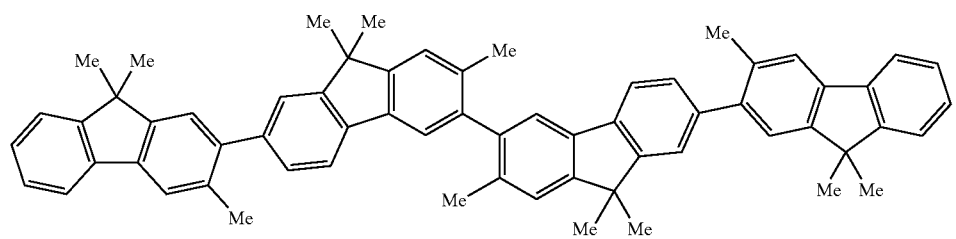
B17
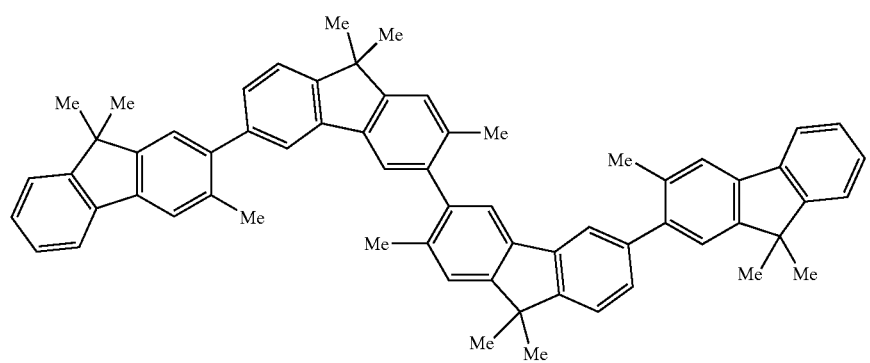
B18
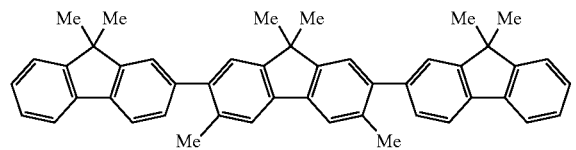
C01
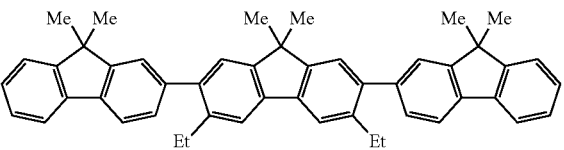
C02
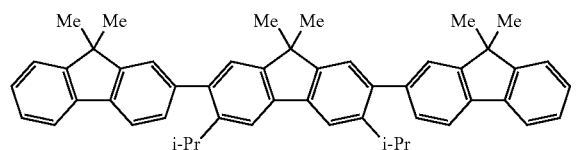
C03
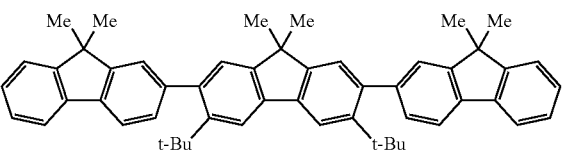
C04

-continued
C05
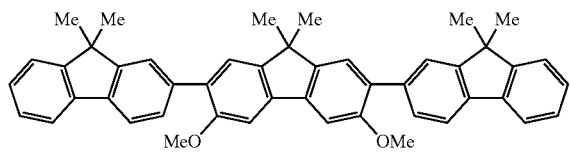
C06
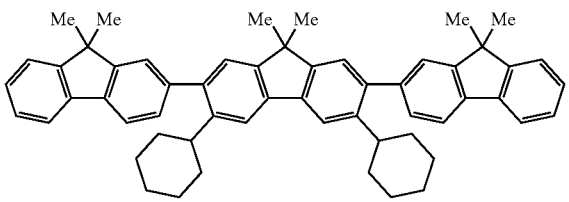
C07
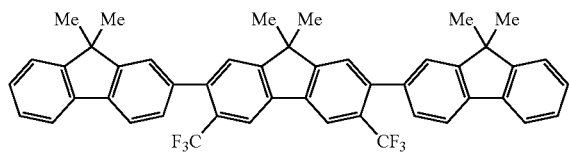
C08
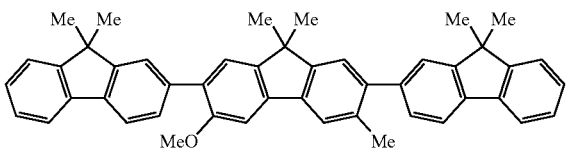
C09
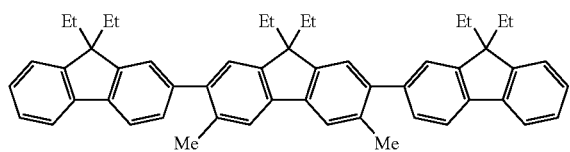
C10
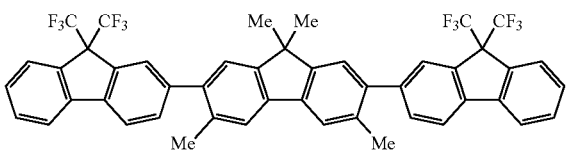
C11
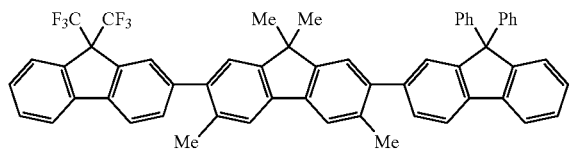
C12
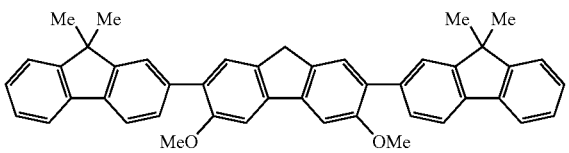
C13
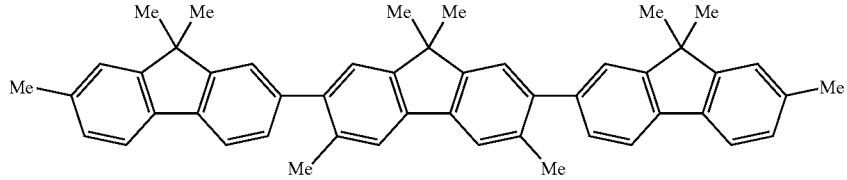
C14
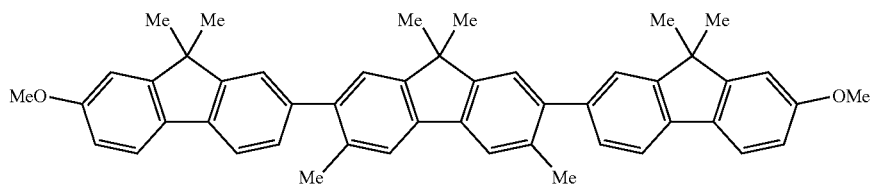
C15
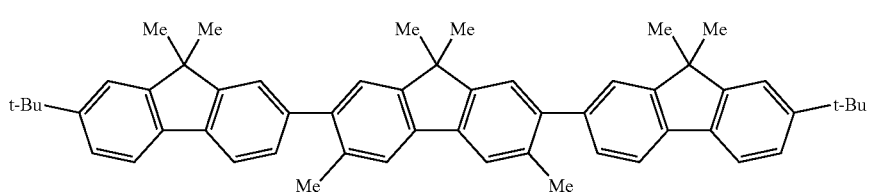
C16
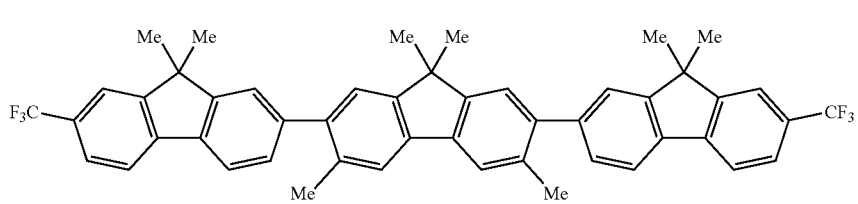

-continued
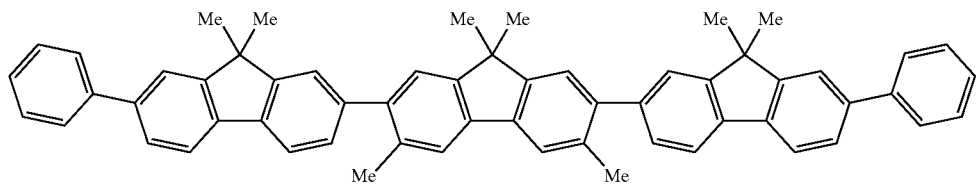
C17
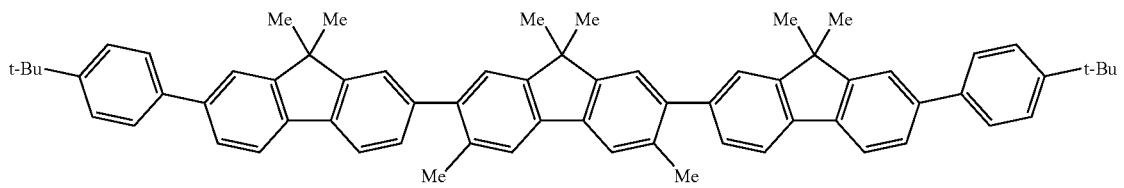
C18
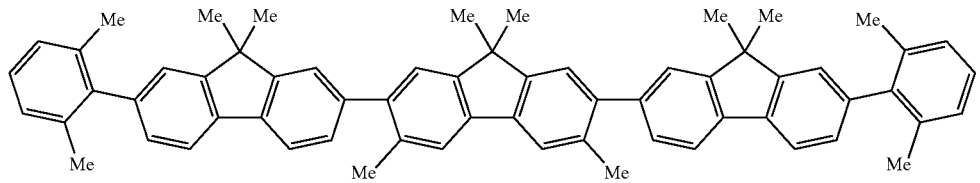
C19
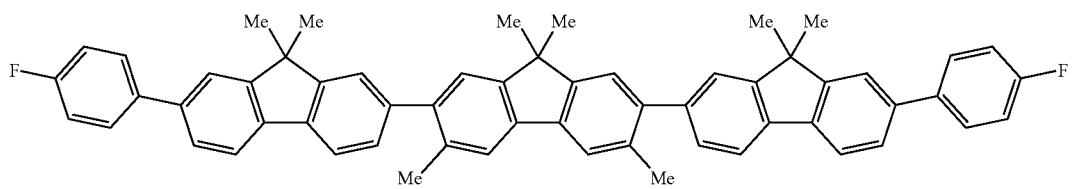
C20
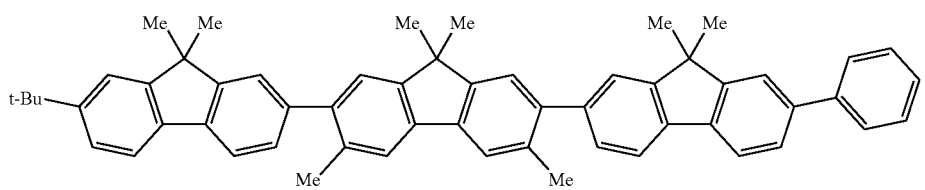
C21
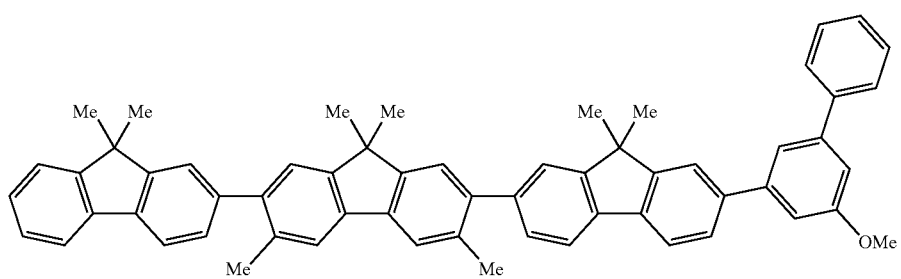
C22
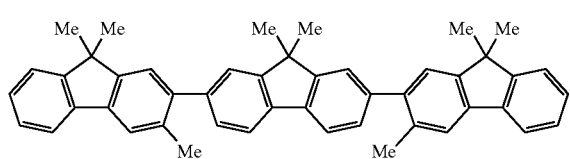
D01
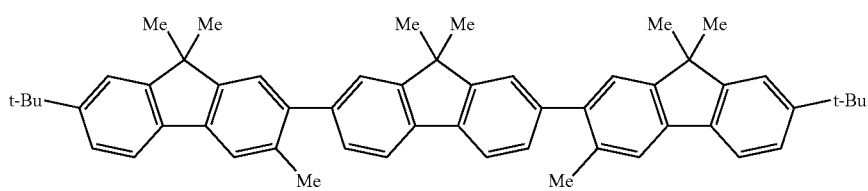
D02

-continued
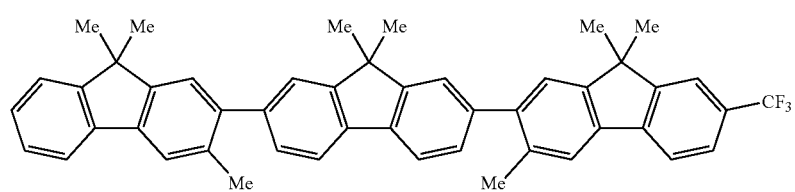
D03
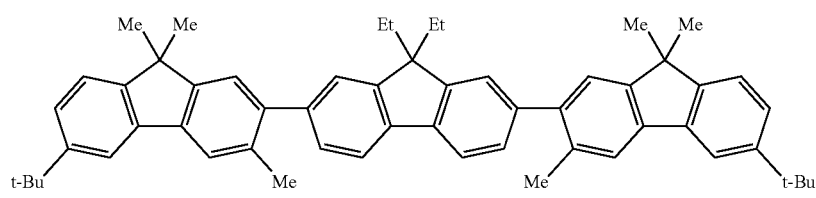
D04
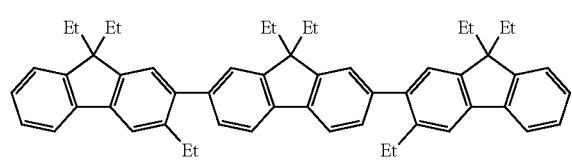
D05
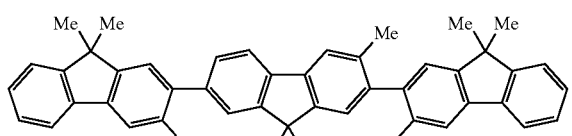
D06
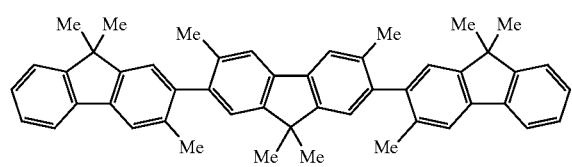
D07
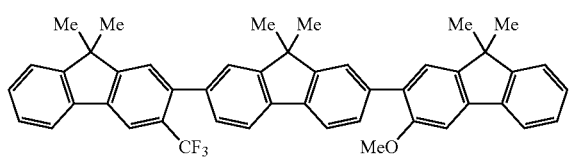
D08
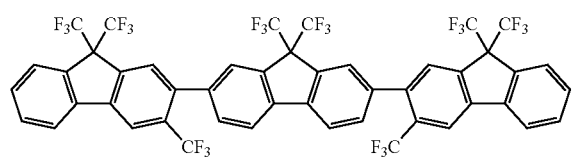
D09
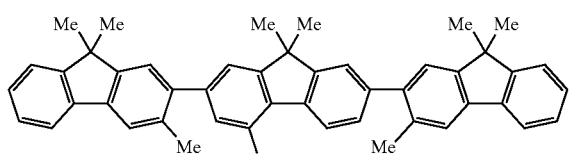
D10
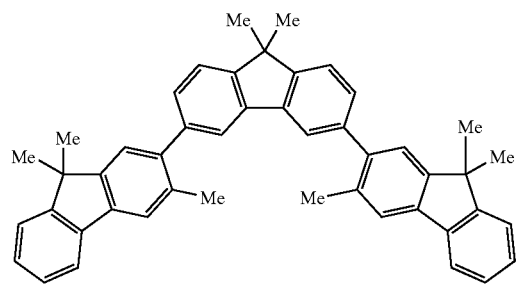
D11
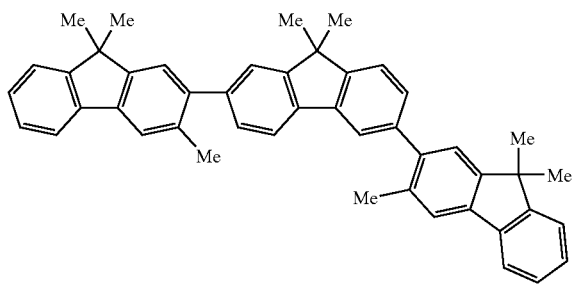
D12
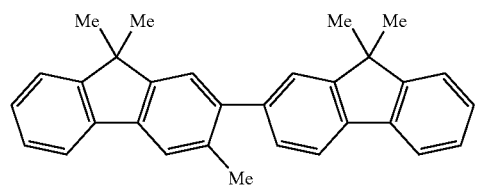
E01
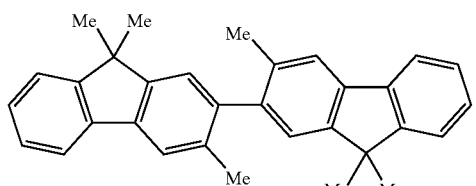
E02
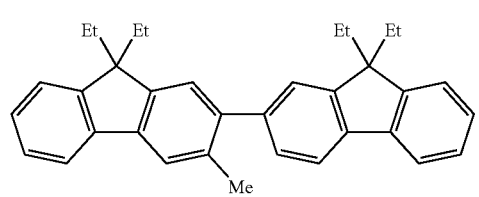
E03
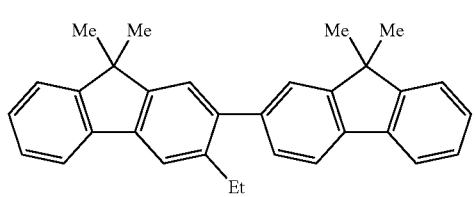
E04

-continued
E05
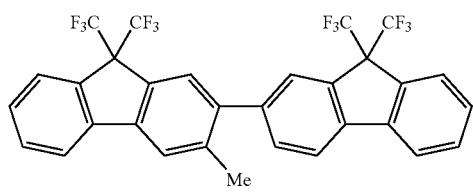
E06
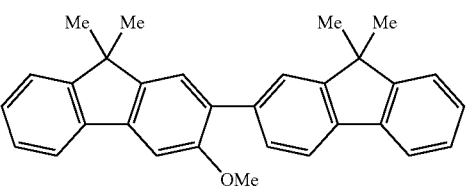
E07
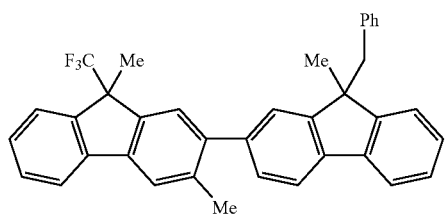
E08
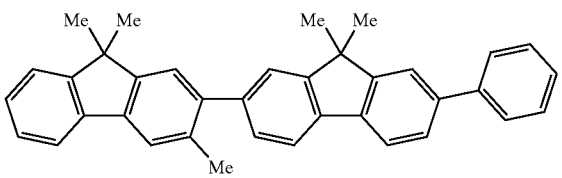
E09
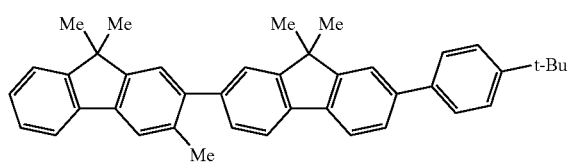
E10
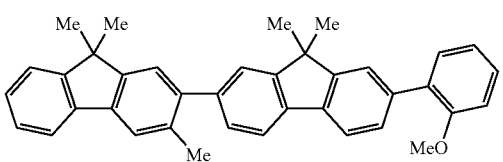
E11
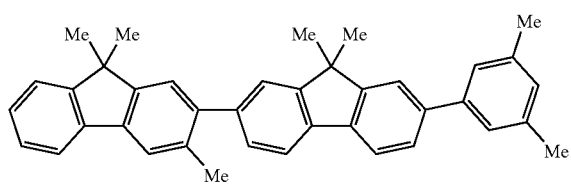
E12
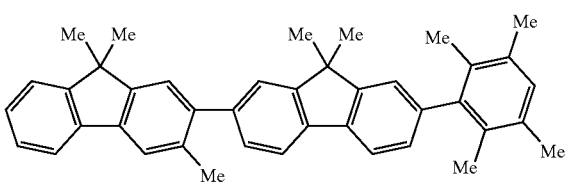
E13
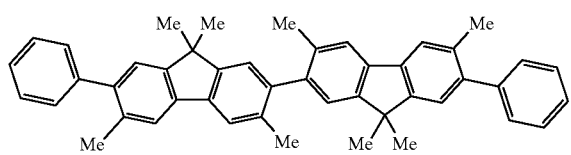
E14
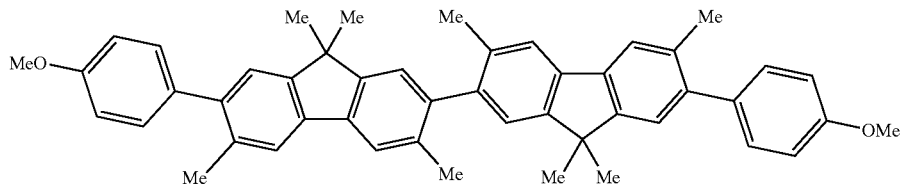
E15
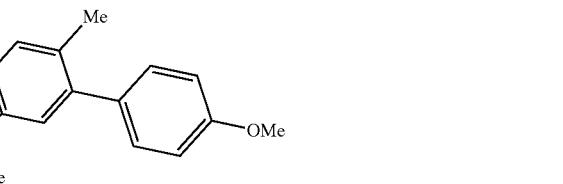
E16
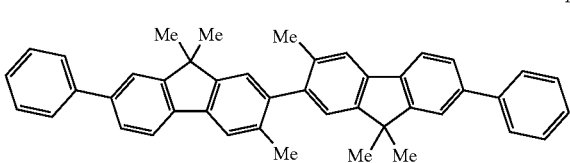
E17
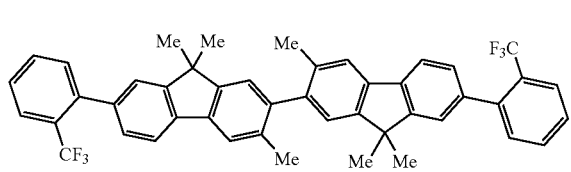

-continued
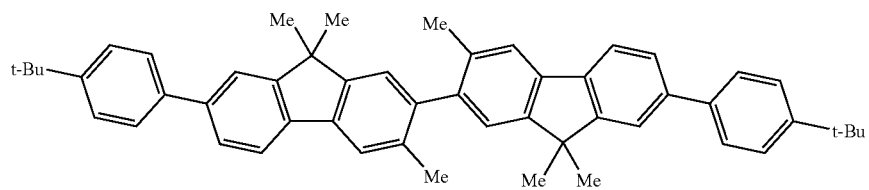
E18
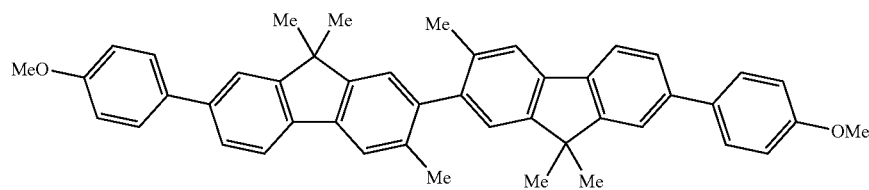
E19
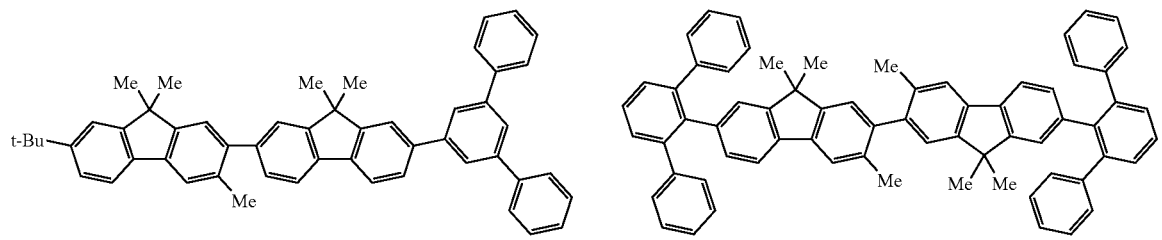
E20  E21
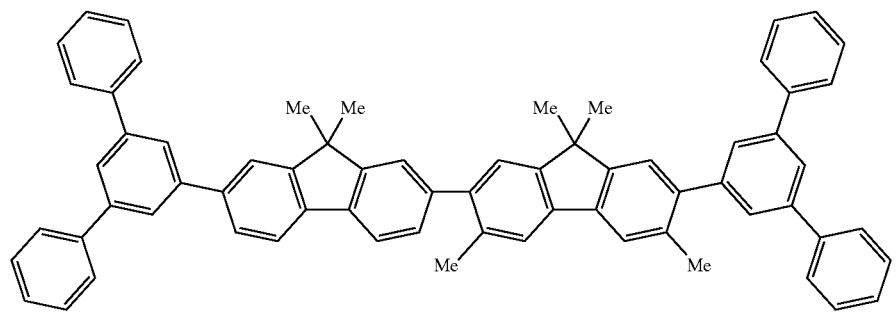
E22
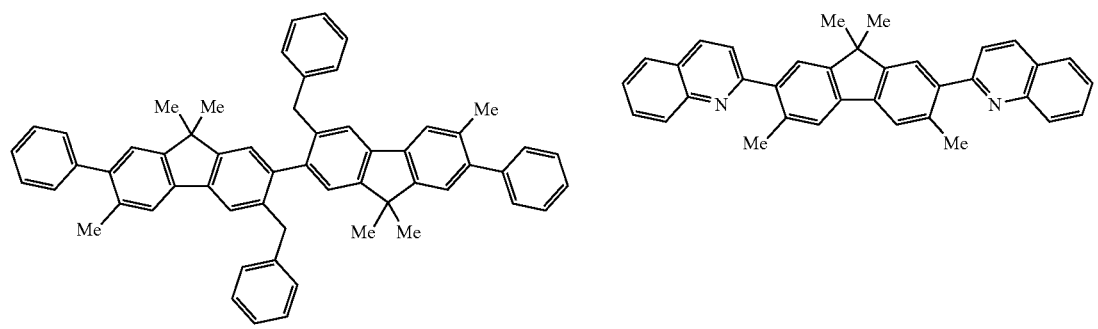
E23  F01
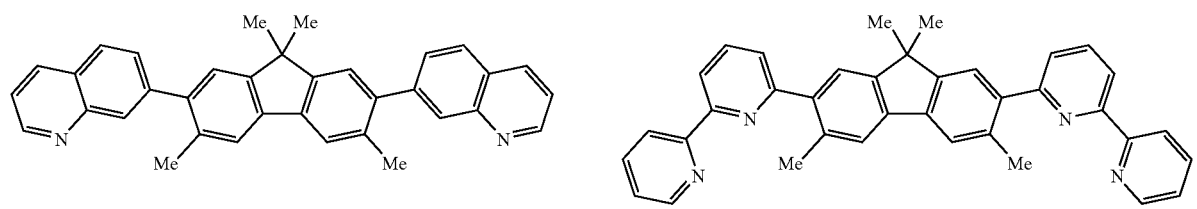
F02  F03

-continued
F04
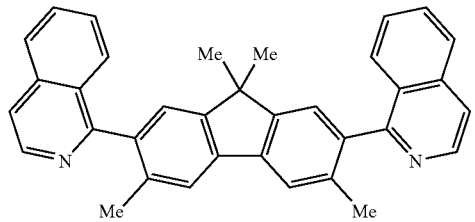
F05
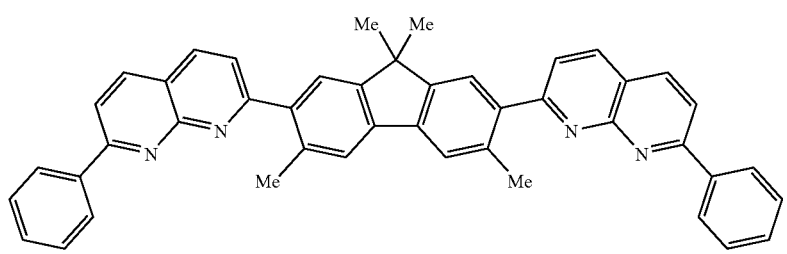
F06
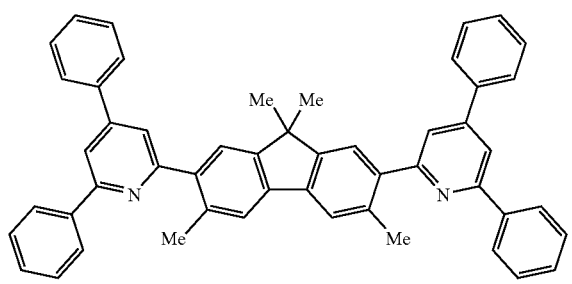
F07
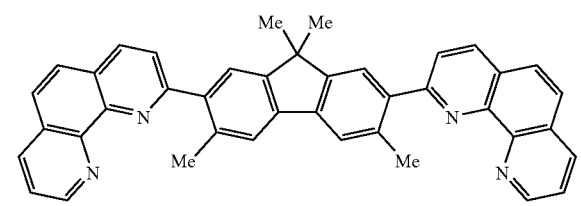
F08
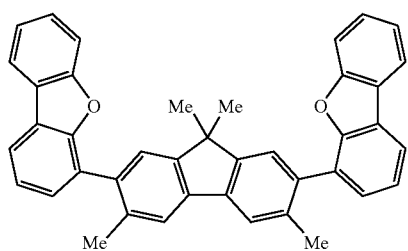
F09
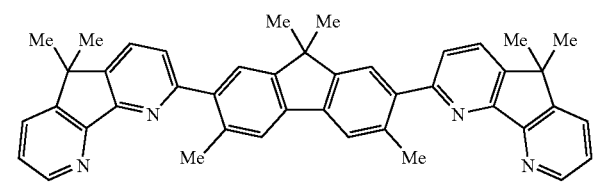
F10
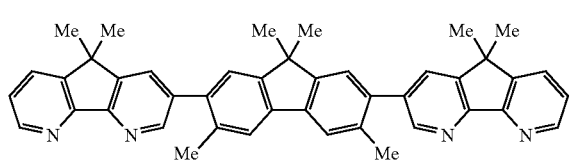
F11
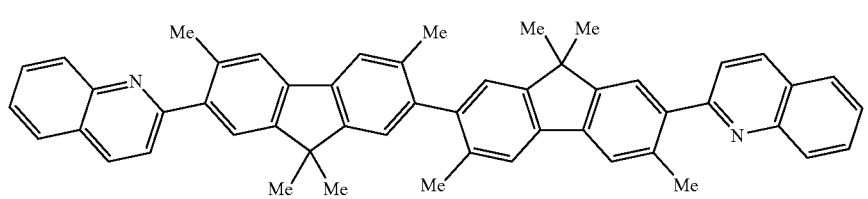

G01
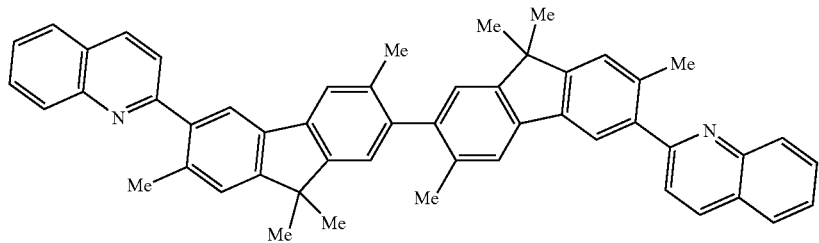
G02
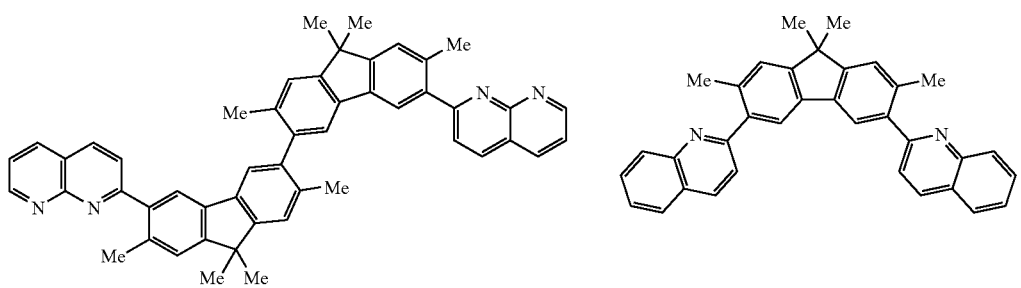
G03
G04
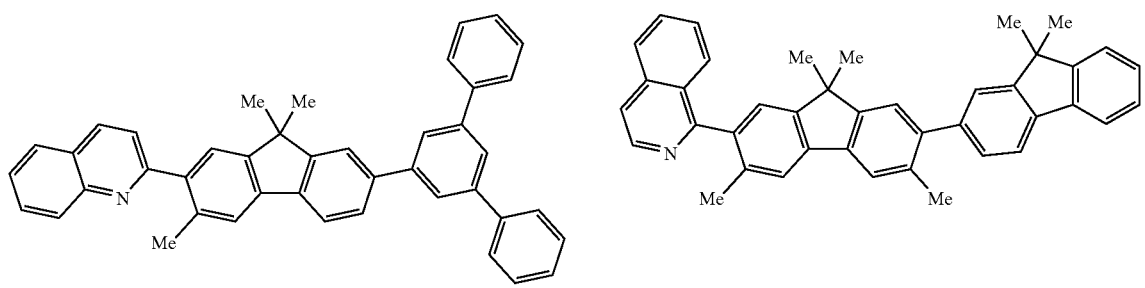
G05
G06
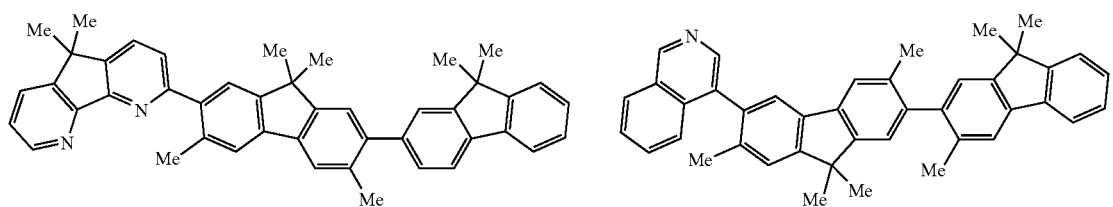
G07
G08
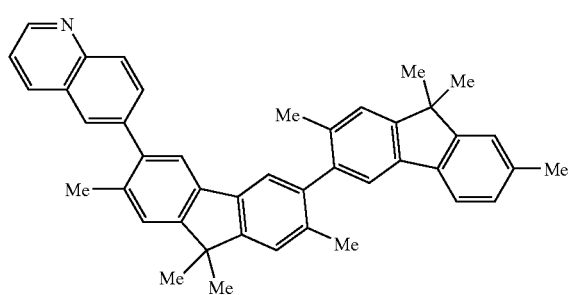
G09
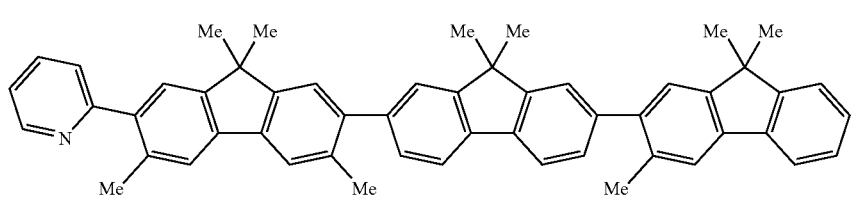

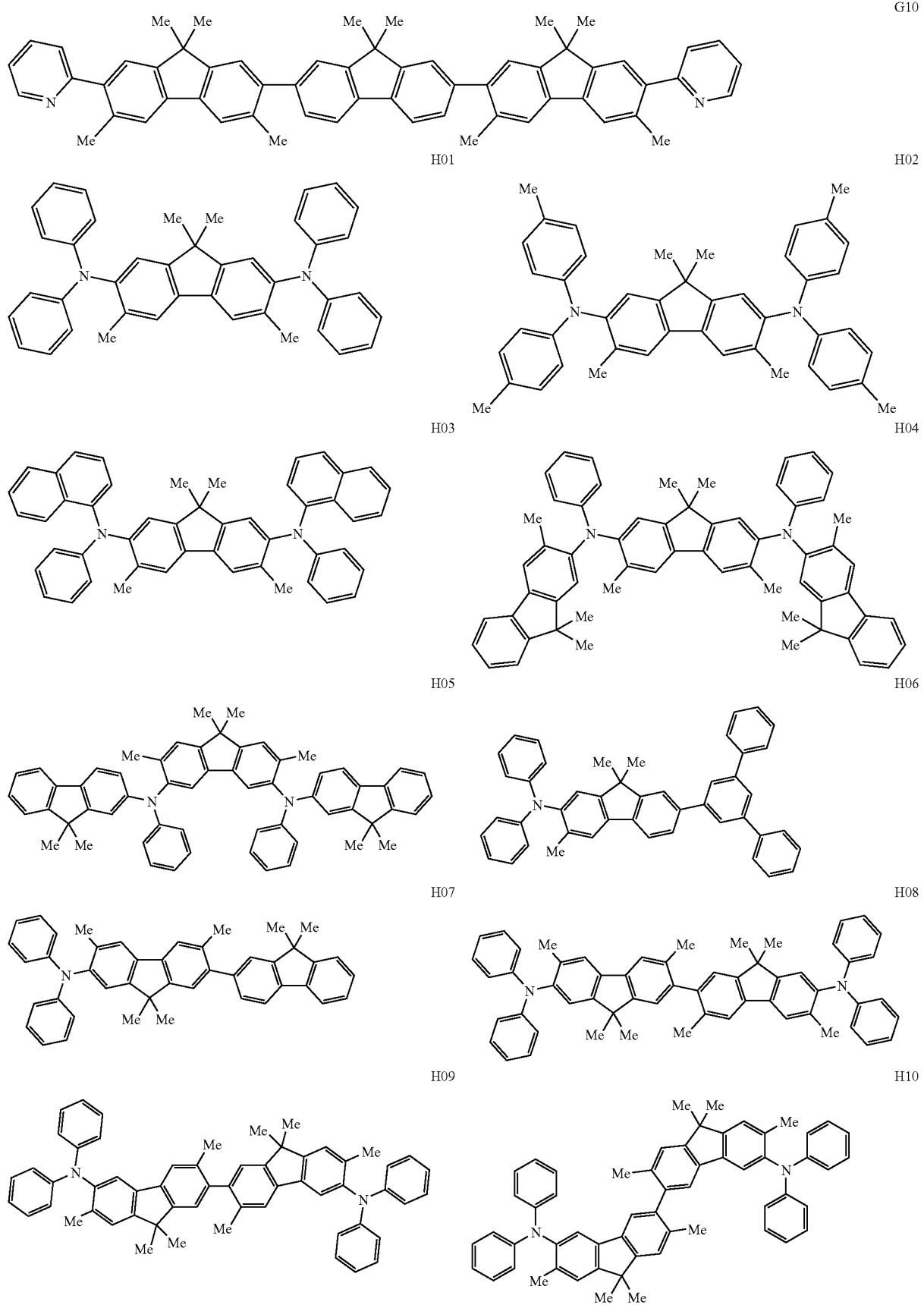

-continued
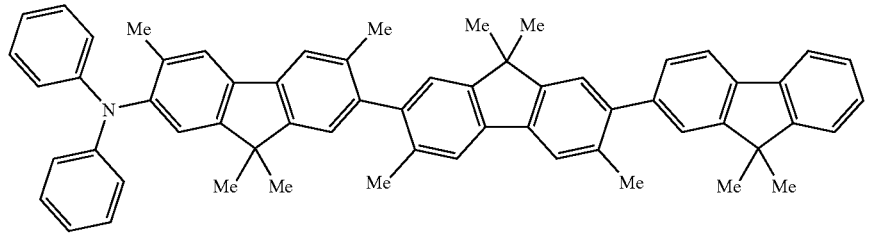
H11
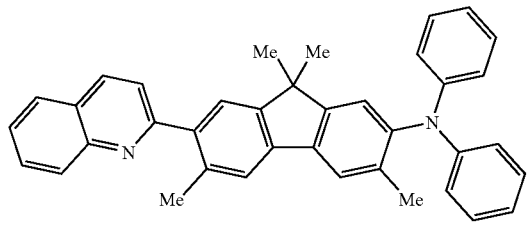
I01
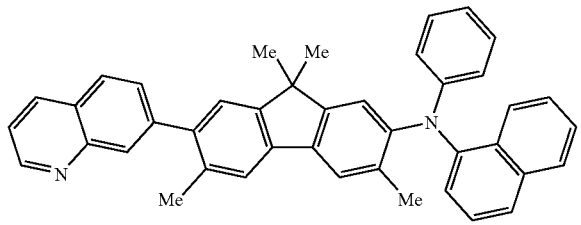
I02
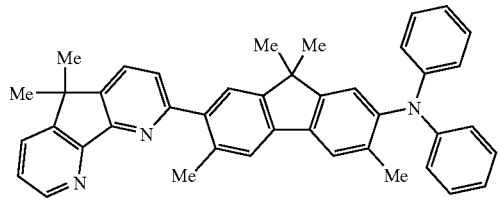
I03
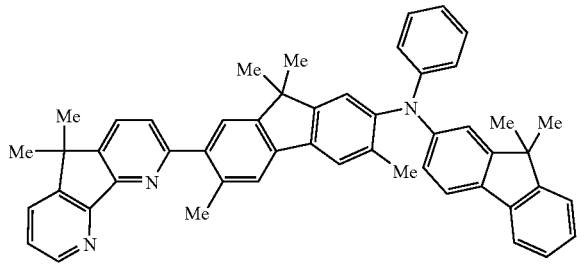
I04
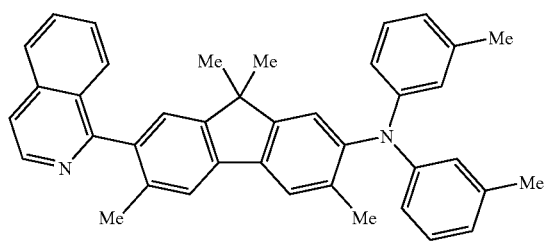
I05
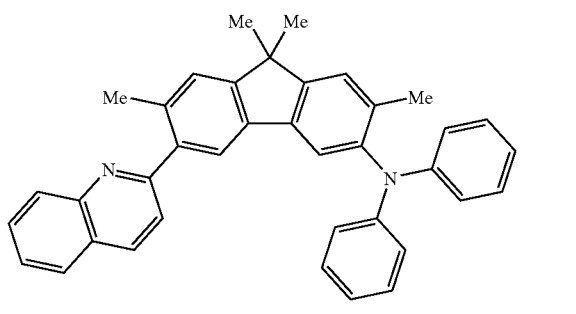
I06
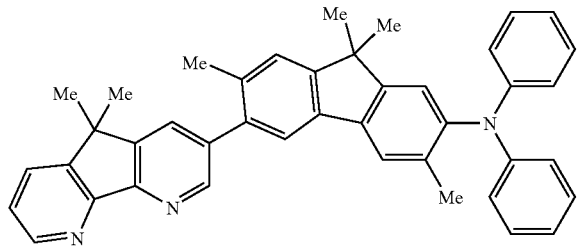
I07
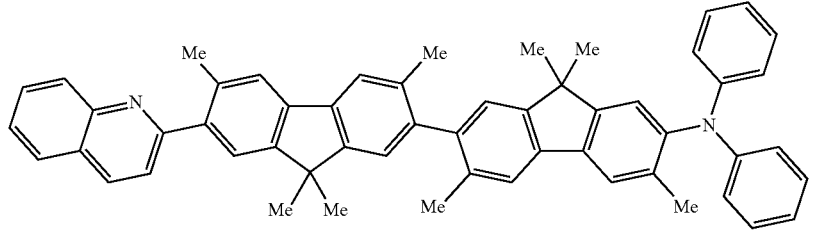
I08

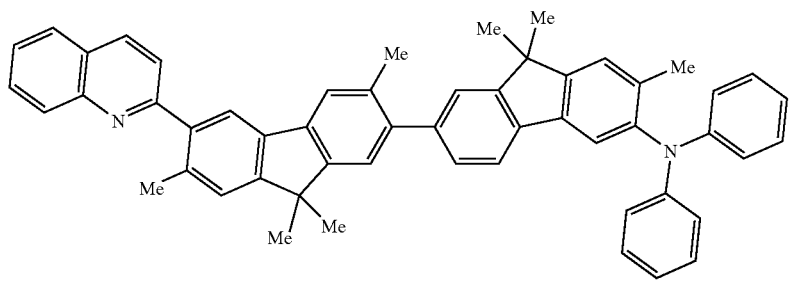

I09

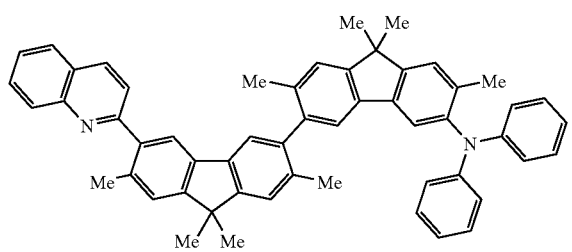

I10

Regarding the organic light-emitting element according to the present invention, it is effective that the above-described fluorene compounds for organic light-emitting elements are used as light-emitting layer hosts. In particular, the fluorene compounds shown in the group A, the group B, the group C, the group D, and the group E of the above-exemplified compounds can be used as light-emitting layer hosts of phosphorescent elements. Furthermore, the fluorene compounds shown in the group I of the above-exemplified compounds can be used as light-emitting layer hosts of phosphorescent elements for serving as bipolar hosts. The fluorene compounds for organic light-emitting elements according to the present invention can also be used as electron transport layers, hole transport layers, electron blocking layers, hole blocking layers, electron injection layers, and hole injection layers other than the light-emitting layers. For example, the fluorene compounds, which include heterocyclic rings, shown in the group F and the group G of the above-exemplified compounds can be used for electron transport layers and electron injection layers. The fluorene compounds, which include substituted amino groups, shown in the group H of the above-exemplified compounds can be used for hole transport layers and hole injection layers.

In the case where the above-described fluorene compounds are used for light-emitting layer hosts in the present invention, generally known fluorescent materials and phosphorescent materials can be used as light-emitting layer guests. In particular, phosphorescent metal complexes, e.g., iridium complexes, platinum complexes, rhenium complexes, copper complexes, europium complexes, and ruthenium complexes, can be used as light-emitting layer guests. The iridium complexes, which emit strong phosphorescence, are more favorable. Furthermore, a plurality of phosphorescent materials can be included in the light-emitting layer for the purpose of emitting the light of a plurality of colors from the light-emitting layer and facilitating the transfer of exciton and charge. The concentration of the light-emitting layer guest compound relative to the light-emitting layer host compound is 0.01 percent by weight to 50 percent by weight, and can be 1 percent by weight to 30 percent by weight. The light-emitting layer guest material may be contained throughout the layer composed of the light-emitting layer host compound uniformly or with a concentration gradient, or be contained partly in a specific region so that some region of the host compound layer may not contain the guest compound.

Specific structural formulae of guest compounds to be used in the present invention will be shown in Table 1, although not limited to them, as a matter of course.

TABLE 1

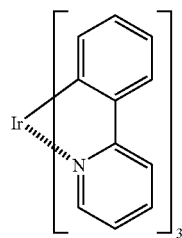

L01

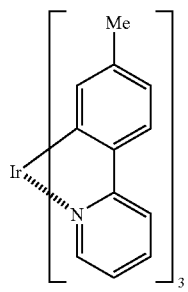

L02

TABLE 1-continued
L03
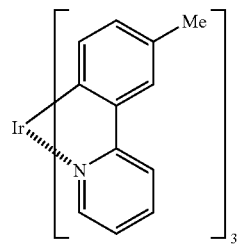
L04
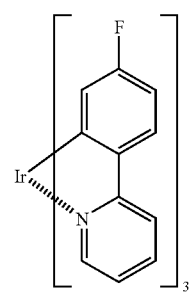
L05
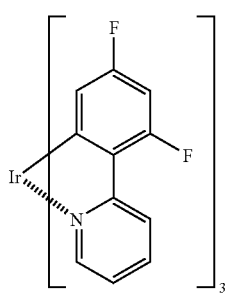
L06
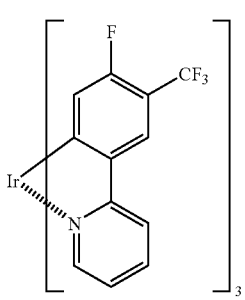
L07
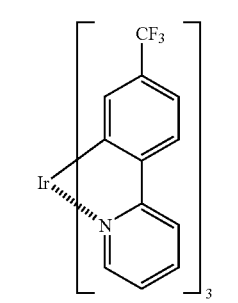
L08
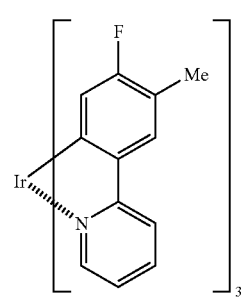
L09
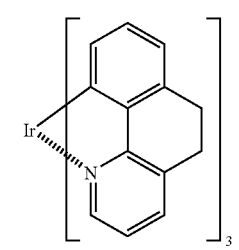
L10
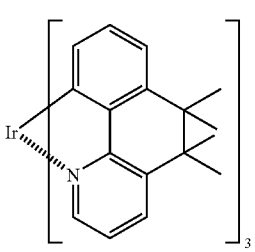
L11
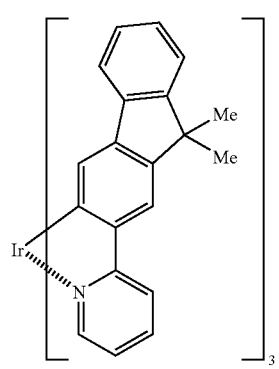
L12
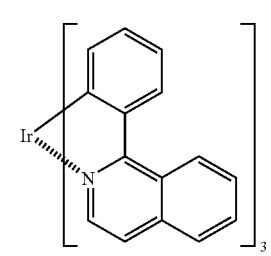

TABLE 1-continued
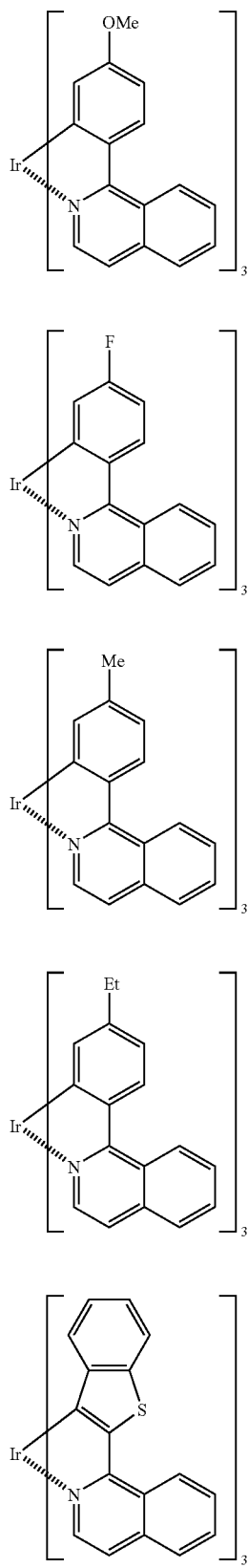
L13
L14
L15
L16
L17
TABLE 1-continued
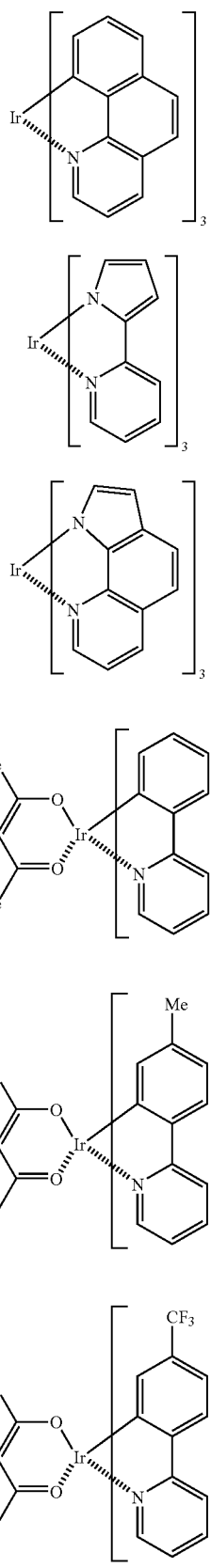
L18
L19
L20
L21
L22
L23

TABLE 1-continued
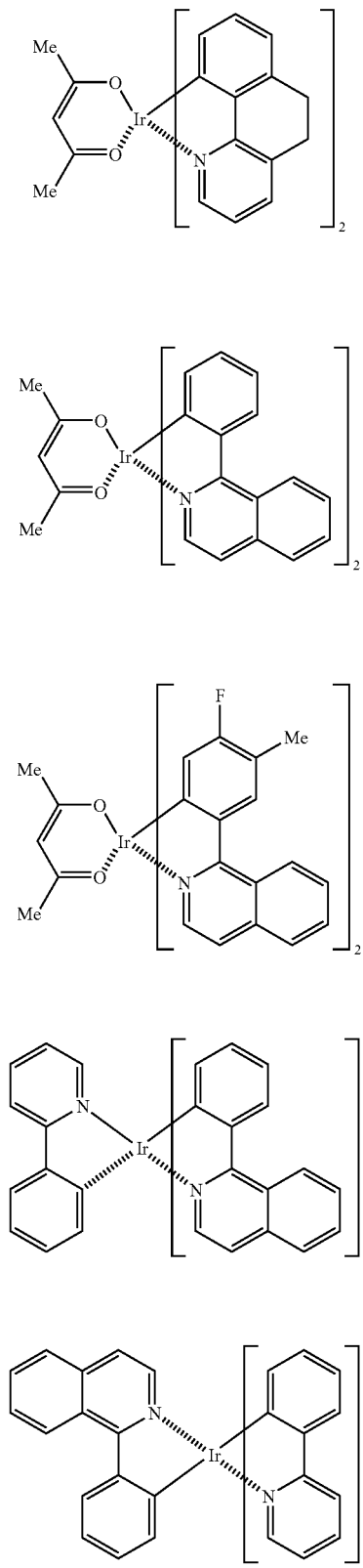
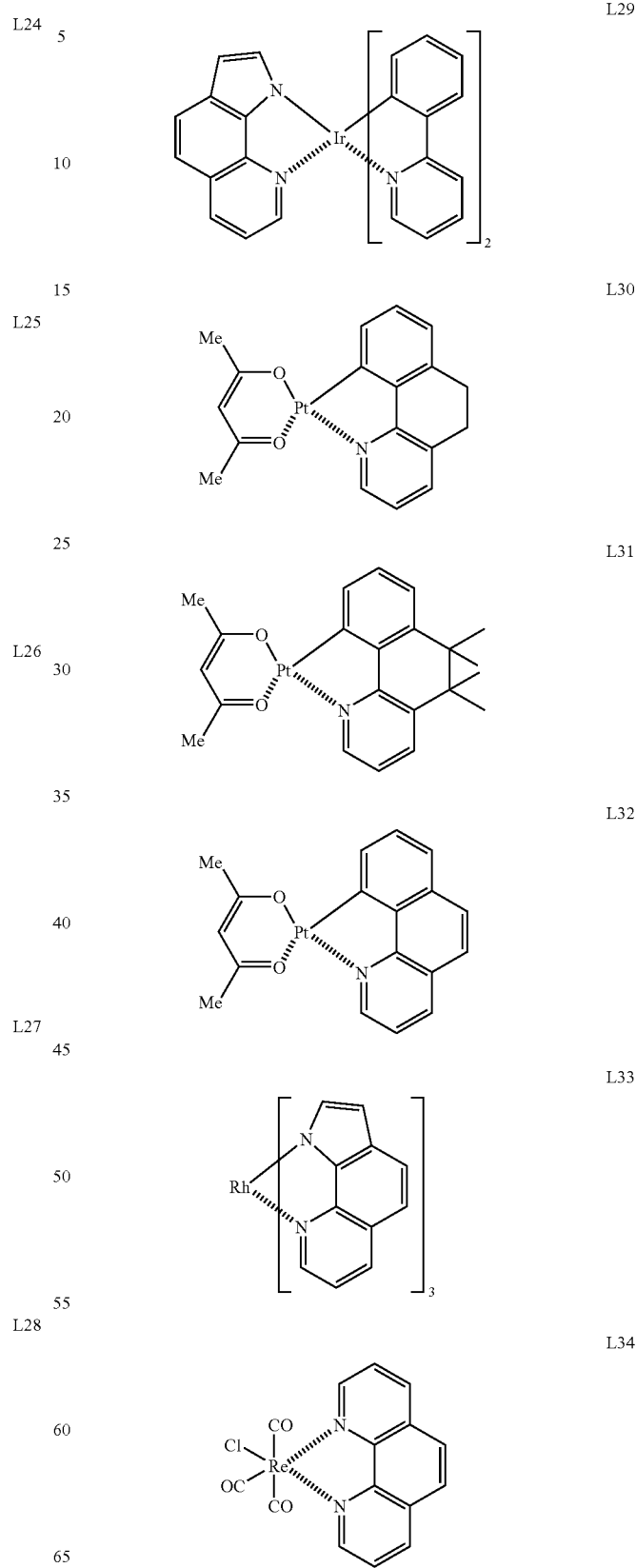

TABLE 1-continued

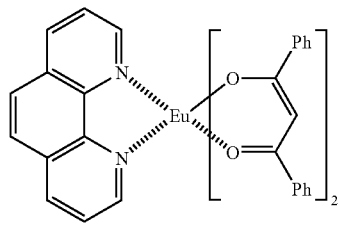

L35

An organic light-emitting element according to the present invention will be described below in detail.

The organic light-emitting element according to the present invention includes at least one pair of electrodes composed of an anode and a cathode and at least one organic-compound-containing layer held between the pair of electrodes, wherein at least one of the above-described organic-compound-containing layers, which can be a light-emitting layer, contains at least one type of the fluorene compounds for organic light-emitting elements represented by General formula [1].

Figure 2:
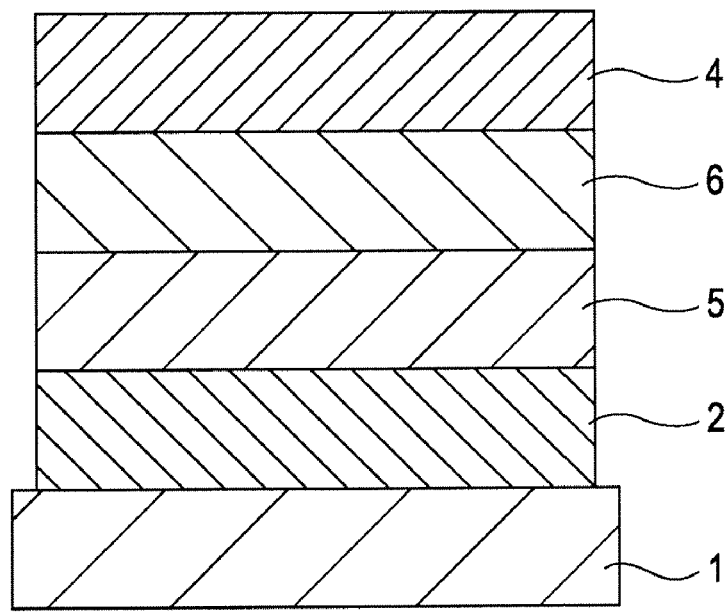
FIG. 2 is a sectional view showing another example of the organic light-emitting element according to the present invention.
Figure 3:
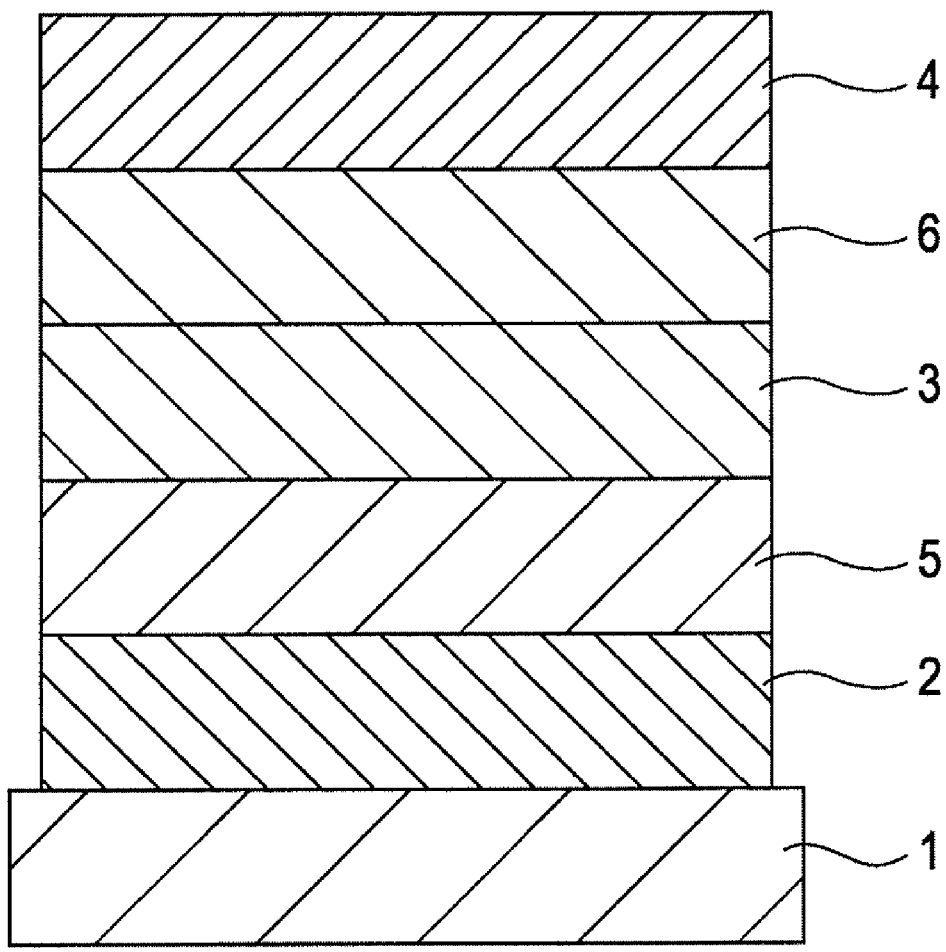
FIG. 3 is a sectional view showing another example of the organic light-emitting element according to the present invention.

FIG. 1 to FIG. 3 show examples of the organic light-emitting element according to the present invention. Reference numeral 1 denotes a substrate, reference numeral 2 denotes an anode, reference numeral 3 denotes a light-emitting layer, reference numeral 4 denotes a cathode, reference numeral 5 denotes a hole transport layer, and reference numeral 6 denotes an electron transport layer.

FIG. 1 is a sectional view showing an example of the organic light-emitting element according to the present invention. FIG. 1 shows a configuration in which the anode 2, the light-emitting layer 3, and the cathode 4 are disposed on the substrate 1 sequentially. The light-emitting element used here is useful in the case where the light-emitting element has the hole transport ability, the electron transport ability, and the light emission property by itself or in the case where compounds having respective characteristics are used by mixing.

FIG. 2 is a sectional view showing another example of the organic light-emitting element according to the present invention. FIG. 2 shows a configuration in which the anode 2, the hole transport layer 5, the electron transport layer 6, and the cathode 4 are disposed on the substrate 1 sequentially. This is useful in the case where a material serving as a light-emitting substance and having any one of or both the hole transport property and the electron transport property is used for the appropriate layer, and merely a hole transport substance or an electron transport substance having no light emission property is used in combination. In this case, the light-emitting element layer is composed of any one of the hole transport layer 5 and the electron transport layer 6.

FIG. 3 is a sectional view showing another example of the organic light-emitting element according to the present invention. FIG. 3 shows a configuration in which the anode 2, the hole transport layer 5, the light-emitting layer 3, the electron transport layer 6, and the cathode 4 are disposed on the substrate 1 sequentially. In this element, functions of carrier transport and light emission are separated. Appropriate combinations with compounds, each having the hole transport property, the electron transport property, or the light-emitting property, are used. Therefore, the degree of flexibility in selection of materials increases significantly, and various compounds for emitting different wavelengths of light can be used, so that the hue of emitted light can be diversified.

Furthermore, it becomes possible to confine each carrier or exciton into the centered light-emitting layer 3 efficiently so as to improve the luminous efficacy as well.

In FIG. 3, a hole injection layer may be inserted between the anode 2 and the hole transport layer 5. In this case, an effect is exerted on an improvement of the adhesion between the anode 2 and the hole transport layer 5 or an improvement of hole injection performance, and it is effective for lowering the voltage.

Furthermore, in FIG. 3, a layer (hole/exciton blocking layer) for inhibiting a hole or an exciton from passing to the cathode 4 side may be inserted between the light-emitting layer 3 and the electron transport layer 6. The use of a compound having a very high ionization potential as the hole/exciton blocking layer is effective for improving the luminous efficacy.

FIG. 1 to FIG. 3 illustrate basic element configurations. The configuration of the organic light-emitting element including the compound according to the present invention is not limited to them. Diverse layer configurations can be adopted. For example, an insulating layer may be disposed at the interface between the electrode and the organic layer, an adhesive layer or an interference layer may be disposed, and the hole transport layer may be composed of two layers having different ionization potentials.

The organic light-emitting element according to the present invention can be used in any one of the forms shown in FIG. 1 to FIG. 3. In the layer containing the fluorene compound represented by General formula [1] according to the present invention, the content of the fluorene compound is preferably 5 percent by weight or more, and can be 70 percent by weight or more, and 100 percent by weight or less.

Furthermore, in the layer formed by a vacuum deposition method, a solution coating method or the like in the present invention, crystallization and the like do not readily occur, so that excellent stability over time is exhibited.

In the present invention, previously known low-molecular-weight and high-molecular-weight compounds having a hole transport property, compounds having a light emission property, compounds having an electron transport property, or the like can also be used together with the fluorene compounds for organic light-emitting elements according to the present invention.

Examples of these compounds will be described below.

A material having high hole mobility can be used as a material having a hole injection and transport property because holes are easily injected from the anode and the injected holes are transported to the light-emitting layer. Examples of low-molecular-weight and high-molecular-weight materials having the hole injection and transport property include triarylamine derivatives, phenylenediamine derivatives, stilbene derivatives, phthalocyanine derivatives, porphyrin derivatives, and poly(vinylcarbazole), poly (thiophene), and other electrically conductive polymers.

Materials having a light emission property and being primarily related to a light emission function include the following compounds (other than the fluorene compounds for the organic light-emitting elements according to the present invention) and guest compounds, as shown in Table 1. Condensed ring compounds (for example, fluorene derivatives, pyrene derivatives, tetracene derivatives, 9,10-diphenylanthracene derivatives, and rubrene), quinacridone derivatives, coumarin derivatives, stilbene derivatives, organic aluminum complexes, e.g., tris(8-quinolinolate) aluminum, organic beryllium complexes, and polymer derivatives, e.g., poly (phenylene vinylene) derivatives, poly(fluorene) derivatives, and poly(phenylene) derivatives, are included, although not limited to them.

The material having an electron injection and transport property can be optionally selected from materials having functions of facilitating injection of electrons from the cathode and transporting the injected electrons to the light-emitting layer. The selection is conducted in consideration of, for example, the balance relative to the carrier mobility of the hole transport material. Examples of materials having the electron injection and transport property include oxadiazole derivatives, oxazole derivatives, pyrazine derivatives, triazole derivatives, triazine derivatives, quinoline derivatives, quinoxaline derivatives, phenanthroline derivatives, diazafluorene derivatives, and organic aluminum complexes, although not limited to them.

In the organic light-emitting element according to the present invention, the layers containing the compound according to the present invention and the layers composed of other organic compounds are formed by the following methods. In general, thin films are formed by a vacuum deposition method, an ion vapor deposition method, sputtering, plasma, or known coating methods (for example, spin coating, dipping, a casting method, an LB method, and an ink-jet method) after dissolution into an appropriate solvent. In particular, in the case where a film is formed by the coating method, the film can also be formed by combining the solution with an appropriate binder resin.

Examples of the above-described binder resins include polyvinylcarbazole resins, polycarbonate resins, polyester resins, ABS resins, acrylic resins, polyimide resins, phenol resins, epoxy resins, silicone resins, and urea resins, although not limited to them. Homopolymers or copolymers of these binder resins may be used alone or at least two types thereof may be mixed. Furthermore, known additives, e.g., plasticizers, antioxidants, and ultraviolet absorbers, may be used in combination in the instant light-emitting element.

An anode material can have a work function as large as possible. For example, simple substances or alloys of metals, e.g., gold, platinum, silver, copper, nickel, palladium, cobalt, selenium, vanadium, and tungsten, and metal oxides, e.g., tin oxide, zinc oxide, indium oxide, indium tin oxide (ITO), and indium zinc oxide, can be used. In addition, electrically conductive polymers, e.g., polyanilines, polypyrroles, and polythiophenes, can also be used. These electrode substances can be used alone or in combination. The anode may have a single-layer configuration or a multilayer configuration.

On the other hand, a cathode material can have a work function as small as possible. Examples thereof include alkali metals, e.g., lithium, alkaline earth metals, e.g., calcium, and simple substances of metals, e.g., aluminum, titanium, manganese, silver, lead, and chromium. Alternatively, a plurality of alloys, e.g., magnesium-silver, aluminum-lithium, and aluminum-magnesium, can be used. Metal oxides, e.g., indium tin oxide (ITO), can also be used. These electrode substances can be used alone or in combination. The cathode may have a single-layer configuration or a multilayer configuration.

The substrate to be used in the present invention is not specifically limited. Typically, opaque substrates, e.g., metal substrates and ceramic substrates, and transparent substrates, e.g., glass, quartz, and plastic sheets, are used. It is possible to control the color of the emitted light by using color filter films, fluorescence color conversion filter films, dielectric reflection films, and the like for the substrate.

Regarding the produced light-emitting element, a protective layer or a sealing layer may be disposed for the purpose of preventing contact with oxygen, water, and the like. Examples of protective layers include inorganic material films, e.g., diamond thin films, metal oxides, and metal nitrides; polymer films, e.g., fluororesins, polyethylenes, silicone resins, and polystyrene resins; and photo-curable resins. The element itself may be packaged by being covered with glass, a gas-impermeable film, a metal, or the like and by using an appropriate sealing resin.

A thin film transistor (TFT) may be produced on a substrate, and the element according to the present invention may be produced while being connected thereto.

Regarding the direction of light emission from the element, a bottom emission configuration (the light is taken out from the substrate side) or a top emission configuration (the light is taken out from the side opposite to the substrate) can be adopted.

EXAMPLES

The present invention will be specifically described below with reference to the following illustrative examples. The present invention is not limited to the illustrative examples.

Example 1

Synthesis of Exemplified Compound D02

(1) Synthesis of Intermediate Compound M2

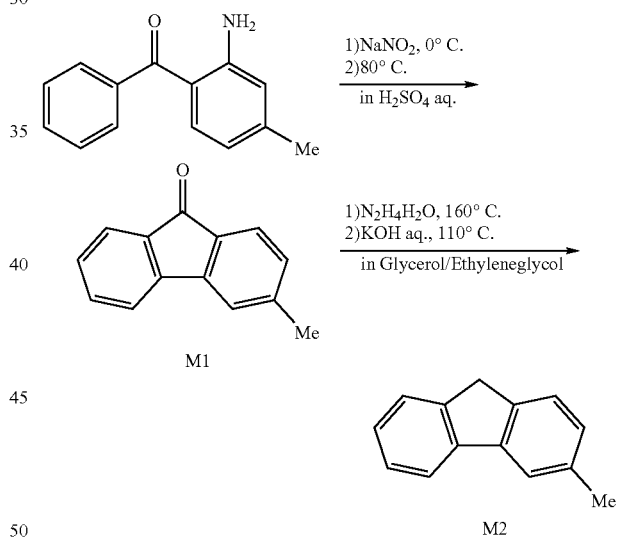

In a nitrogen atmosphere, 3.34 g (15.8 mmol) of 2-amino-4-methylbenzophenone was dissolved into a mixed solvent of water (24 mL)/concentrated sulfuric acid (12 mL), and an aqueous solution, in which 2.0 g (29.0 mmol) of sodium nitrite was dissolved into 30 mL of water, was added thereto by using a dropping funnel with agitation at 0° C. Subsequently, the reaction solution was heated at 80° C. for 2.5 hours with agitation. After the reaction, the resulting product was extracted with chloroform, and the resulting chloroform phase was washed with dilute hydrochloric acid, a sodium carbonate aqueous solution, and pure water, sequentially, followed by concentration. Refining was conducted with an aluminum column (mixed developing solvent of heptane/toluene=1/1), so that 2.14 g of Intermediate compound M1 [3-methylfluoren-9-one] was obtained (yield 70%).

Thereafter, 2.13 g (11.0 mmol) of Intermediate compound M1 was dissolved into a 43 mL of mixed solvent of glycerol/ethylene glycol=1/1, and, thereafter, 3.2 mL (65.8 mmol) of hydrazine monohydrate was added. Heating was conducted at 80° C. for 90 minutes with agitation and, furthermore, heating with reflux was conducted at 162° C. for 80 minutes. After cooling to 60° C., an aqueous solution, in which 3.7 g (65.8 mmol) of potassium hydroxide was dissolved into 15.4 mL of water, was completely added, and heating with reflux was conducted again at 110° C. for 2 hours. After the reaction, the resulting product was precipitated by adding 200 mL of water. The product was recovered by filtration and was washed with water and methanol, so that 1.82 g of Intermediate Compound M2 [3-methyl-9H-fluorene] was obtained (yield 92%).

(2) Synthesis of Intermediate Compound M4

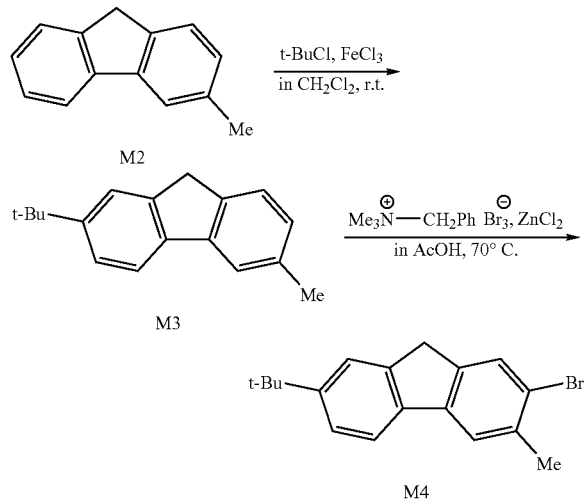

In a nitrogen atmosphere, 1.81 g (10.0 mmol) of Intermediate compound M2 and 1.56 mL (14.2 mmol) of tert-butyl chloride were dissolved into 35 mL of dehydrated dichloromethane, and the reaction was conducted for 90 minutes at room temperature with agitation while 0.53 g (3.27 mmol) of ion(III) chloride was added slowly. Subsequently, 200 mL of water was added so as to terminate the reaction, and an organic phase was extracted with toluene. The resulting product was washed three times with 10-percent hydrochloric acid and two times with pure water, and was dried with magnesium sulfate. Refining was conducted with a silica gel column (mixed developing solvent of heptane/toluene=100/1), so that 1.81 g of Intermediate compound M3 [2-tert-butyl-6-methyl-9H-fluorene] was obtained (yield 76%).

Thereafter, in a nitrogen atmosphere, 1.62 g (6.86 mmol) of Intermediate compound M3 and 2.68 g (6.87 mmol) of benzyltrimethylammonium tribromide were dissolved into 70 mL of acetic acid, and 0.94 g (6.86 mmol) of zinc chloride was added slowly. Heating with agitation was conducted at 70° C. for 2 hours. After cooling, the reaction was terminated by adding water, so that crystals of the product were precipitated. The crystals were recovered by filtration and were washed with methanol while being dispersed, so that 1.96 g of Intermediate compound M4 [2-bromo-7-tert-butyl-3-methyl-9H-fluorene] was obtained (yield 91%).

(3) Synthesis of Intermediate Compound M5

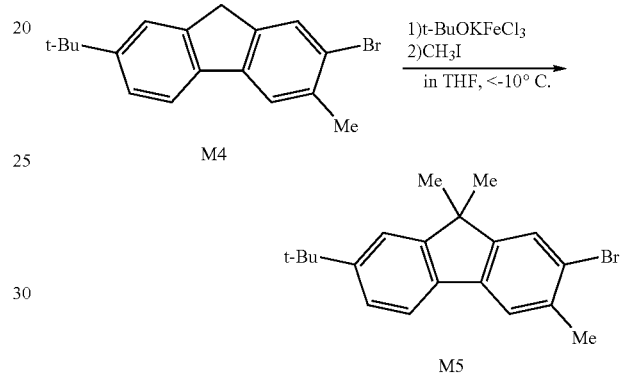

In a nitrogen atmosphere, 1.95 g (6.19 mmol) of Intermediate compound M4 and 2.08 g (18.6 mmol) of tert-butoxy potassium were dissolved into 20 mL of THF. Subsequently, a solution, in which 0.96 mL (15.5 mmol) of iodomethane was diluted with 5 mL of THF, was dropped thereto with agitation at −10° C. over 1 hour. The agitation was further conducted for 2 hours and, thereafter, the reaction was terminated by adding water. The precipitate was recovered by filtration and was washed with a mixed solvent of methanol/acetone while being dispersed, so that 1.92 g of Intermediate compound M5 [2-bromo-7-tert-butyl-3,9,9-trimethyl-9H-fluorene] was obtained (yield 91%).

(4) Synthesis of Exemplified Compound D02

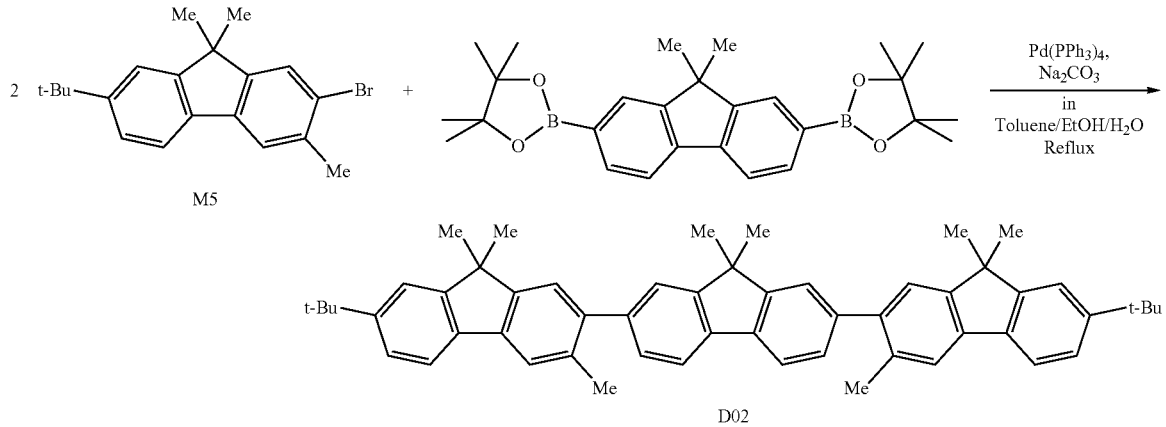

In a nitrogen atmosphere, 0.70 g (2.04 mmol) of Intermediate compound M5, 0.43 g (0.97 mmol) of 2,7-bis(4,4,5,5-tetramethyl[1,3,2]dioxaborolane-2-yl)-9,9-dimethyl-9H-fluorene, and 0.112 g (0.097 mmol) of tetrakis(triphenylphosphine)palladium were added to a mixed solvent of toluene (36 mL)/ethanol (18 mL) and, furthermore, 17 mL of 10 percent by weight sodium carbonate aqueous solution was added. Heating with reflux was conducted at 67° C. for 5 hours with agitation. After the reaction, an organic phase was extracted with toluene, washed with water so as to be concentrated, and refined with a silica gel column (mixed developing solvent of heptane/toluene=3/1). Vacuum drying was conducted at 140° C. and, furthermore, refining by sublimation was conducted, so that 517 mg of Exemplified compound D02 was obtained (yield 74%).

It was ascertained on the basis of the matrix assisted laser desorption/ionization-time of flight mass spectrometry (MALDI-TOF-MS) that M$^+$ of this compound was 718.5, where M$^+$ means a mass of molecular ion. Furthermore, the structure was also ascertained on the basis of the $^1$H-NMR measurement.

Example 2

Synthesis of Exemplified Compound C01

(1) Synthesis of Intermediate Compound M6

Intermediate compound M6 [3,6-dimethyl-9H-fluorene] was obtained in a manner similar to that in Example 1-(1) except that 2-amino-4,4'-dimethylbenzophenone was used instead of 2-amino-4-methylbenzophenone in Example 1-(1).

(2) Synthesis of Intermediate Compound M8

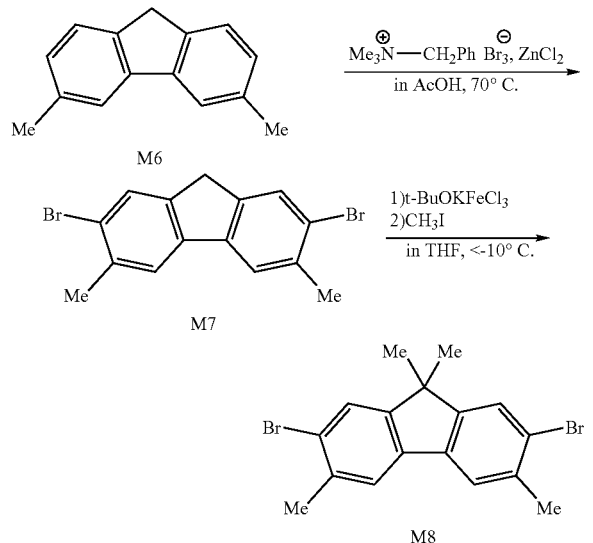

In a manner similar to that in Example 1-(2), 7.02 g (yield 97%) of Intermediate compound M7 [2,7-dibromo-3,6-dimethyl-9H-fluorene] was obtained by using 4.00 g (20.6 mmol) of Intermediate compound M6, 16.6 g (42.6 mmol) of benziltrimethylammonium tribromide, and 5.90 g (42.6 mmol) of zinc chloride.

Subsequently, in a manner similar to that in Example 1-(3), 6.35 g (yield 85%) of Intermediate compound M8 [2,7-dibromo-3,6,9,9-tetramethyl-9H-fluorene] was obtained by using 6.91 g (19.6 mmol) of Intermediate compound M7, 6.60 g (58.9 mmol) of tert-butoxy potassium, and 3.06 mL (49.2 mmol) of iodomethane.

(3) Synthesis of Exemplified Compound C01

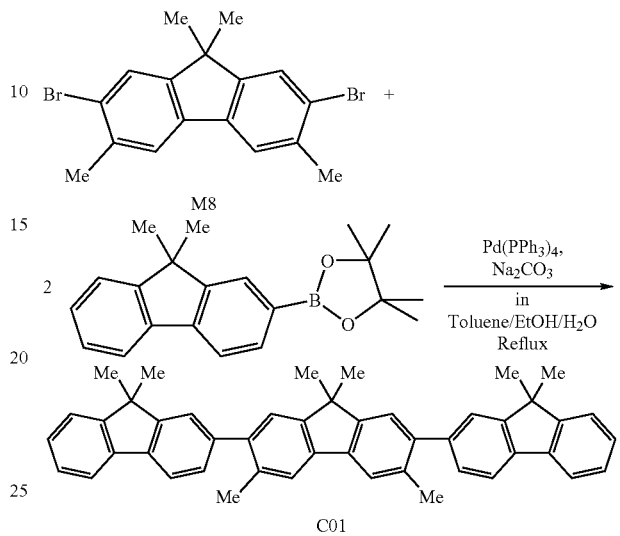

In a nitrogen atmosphere, 0.50 g (1.32 mmol) of Intermediate compound M8, 0.93 g (2.89 mmol) of 2-(9,9-dimethyl-9H-fluorene-2-yl)-4,4,5,5-tetramethyl[1,3,2]dioxaborolane, and 0.152 g (0.13 mmol) of tetrakis(triphenylphosphine)palladium were added to a mixed solvent of toluene (35 mL)/ethanol (12 mL) and, furthermore, 12 mL of 10 percent by weight sodium carbonate aqueous solution was added. Heating with reflux was conducted at 68° C. for 6 hours with agitation. After the reaction, an organic phase was extracted with toluene, washed with water so as to be concentrated, and refined with a silica gel column (mixed developing solvent of heptane/toluene=3/1). Vacuum drying was conducted at 140° C. and, furthermore, refining by sublimation was conducted, so that 584 mg of Exemplified compound C01 was obtained (yield 73%).

It was ascertained on the basis of the matrix assisted laser desorption/ionization-time of flight mass spectrometry (MALDI-TOF-MS) that M$^+$ of this compound was 606.3. Furthermore, the structure was also ascertained on the basis of the $^1$H-NMR measurement.

Example 3

Synthesis of Exemplified Compound F01

(1) Synthesis of Intermediate Compound M9

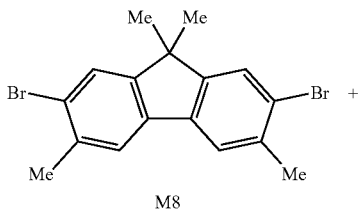

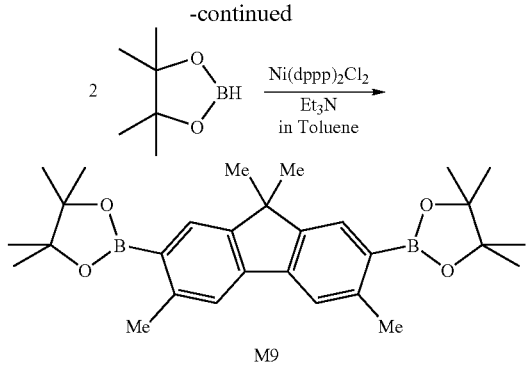

In a nitrogen atmosphere, 2.00 g (5.26 mmol) of Intermediate compound M8 and 0.87 g (1.60 mmol) of (1,3-bis[diphenylphosphino]propane)dichloronickel(II) were dissolved into 80 mL of dehydrated toluene. Subsequently, 3.66 mL (26.4 mmol) of trimethylamine and 3.83 mL (26.4 mmol) of 4,4,5,5-tetramethyl-[1,3,2]dioxaborolane were added, and heating was conducted at 90° C. for 20 hours with agitation. After cooling to room temperature, the reaction was terminated by adding water. The reaction solution was filtrated so as to remove impurities. The product in the filtrate was extracted with toluene, washed with water so as to be concentrated, and refined with a silica gel column (mixed developing solvent of heptane/toluene=1/1), so that 827 mg of Intermediate compound M9 [2,7-bis(4,4,5,5-tetramethyl[1,3,2]dioxaborolane-2-yl)-3,6,9,9-tetramethyl-9H-fluorene] was obtained (yield 33%).

(2) Synthesis of Exemplified Compound F01

Exemplified compound F01 can be synthesized in a manner similar to that in Example 1-(4) except that 2-chloroquinoline is used instead of Intermediate compound M5 and Intermediate compound M9 is used instead of 2,7-bis(4,4,5,5-tetramethyl[1,3,2]dioxaborolane-2-yl)-9,9-dimethyl-9H-fluorene in Example 1-(4).

Example 4

Synthesis of Exemplified Compound G05

(1) Synthesis of Intermediate Compound M10

Intermediate compound M10 [2-bromo-7-(4,4,5,5-tetramethyl[1,3,2]dioxaborolane-2-yl)-3,6,9,9-tetramethyl-9H-fluorene] can be synthesized in a manner similar to that in Example 3-(1) except that the equivalent amounts of triethylamine and 4,4,5,5-tetramethyl-[1,3,2]dioxaborolane are reduced to half and the heating and reaction time is reduced in Example 3-(1).

(2) Synthesis of Intermediate Compound M11

Intermediate compound M11 [2 bromo-7-(isoquinoline-1-yl)-3,6,9,9-tetramethyl-9H-fluorene] can be synthesized in a manner similar to that in Example 1-(4) except that 1-chloroisoquinoline is used instead of Intermediate compound M5 and Intermediate compound M10 is used instead of 2,7-bis(4,4,5,5-tetramethyl[1,3,2]dioxaborolane-2-yl)-9,9-dimethyl-9H-fluorene in Example 1-(4).

(3) Synthesis of Exemplified Compound G05

Exemplified compound G05 can be synthesized in a manner similar to that in Example 2-(3) except that Intermediate compound M11 is used instead of Intermediate compound M8 in Example 2-(3).

Example 5

Synthesis of Exemplified Compound H01

Exemplified compound H01 can be synthesized by conducting an amination reaction in a xylene solvent by using Intermediate compound M8, diphenylamine, bis(dibenzylideneacetone)dipalladium, tri-tert-butylphosphine, and tert-butoxy potassium in a manner similar to the method described in J. Org. Chem., 64, 5575 (1999).

Example 6

Synthesis of Exemplified Compound H07

(1) Synthesis of Intermediate Compound M12

Intermediate compound M12 [2 bromo-7-(9,9-dimethyl-9H-fluorene-2-yl)-3,6,9,9-tetramethyl-9H-fluorene] can be synthesized in a manner similar to that in Example 1-(4) except that 2-iode-9,9-dimethyl-9H-fluorene is used instead of Intermediate compound M5 and Intermediate compound M10 is used instead of 2,7-bis(4,4,5,5-tetramethyl[1,3,2]dioxaborolane-2-yl)-9,9-dimethyl-9H-fluorene in Example 1-(4).

(2) Synthesis of Exemplified Compound H07

Exemplified compound H07 can be synthesized in a manner similar to that in Example 5 except that Intermediate compound M12 is used instead of Intermediate compound M8 in Example 5.

Example 7

Synthesis of Exemplified Compound I01

(1) Synthesis of Intermediate Compound M13

Intermediate compound M13 [2-bromo-7-(quinoline-2-yl)-3,6,9,9-tetramethyl-9H-fluorene] can be synthesized in a manner similar to that in Example 1-(4) except that 2-chloroquinoline is used instead of Intermediate compound M5 and Intermediate compound M10 is used instead of 2,7-bis(4,4,5,5-tetramethyl[1,3,2]dioxaborolane-2-yl)-9,9-dimethyl-9H-fluorene in Example 1-(4).

(2) Synthesis of Exemplified Compound I01

Exemplified compound I01 can be synthesized in a manner similar to that in Example 5 except that Intermediate compound M13 is used instead of Intermediate compound M8 in Example 5.

Example 8

Synthesis of Exemplified Compound C17

(1) Synthesis of Intermediate Compound M14

Intermediate compound M14 [2-bromo-7-phenyl-9,9-dimethyl-9H-fluorene] can be synthesized in a manner similar to that in Example 2-(3) except that 2-bromo-7-iode-9,9-dimethyl-9H-fluorene is used instead of Intermediate compound M8 and phenylboronic acid is used instead of 2-(9,9-dimethyl-9H-fluorene-2-yl)-4,4,5,5-tetramethyl[1,3,2]dioxaborolane in Example 2-(3).

(2) Synthesis of Exemplified Compound C17

Exemplified compound C17 can be synthesized in a manner similar to that in Example 1-(4) except that Intermediate compound M14 is used instead of Intermediate compound M5 and Intermediate compound M9 is used instead of 2,7- bis(4,4,5,5-tetramethyl[1,3,2]dioxaborolane-2-yl)-9,9-dimethyl-9H-fluorene in Example 1-(4).

Example 9

Synthesis of Exemplified Compound E14

(1) Synthesis of Intermediate Compound M15

Intermediate compound M15 [2-bromo-7-(4-methoxyphenyl)-3,6,9,9-tetramethyl-9H-fluorene] can be synthesized in a manner similar to that in Example 2-(3) except that 4-methoxyphenylboronic acid is used instead of 2-(9,9-dimethyl-9H-fluorene-2-yl)-4,4,5,5-tetramethyl[1,3,2]dioxaborolane in Example 2-(3).

(2) Synthesis of Intermediate Compound M16

Intermediate compound M16 [2-(7-(4-methoxyphenyl)-3,6,9,9-tetramethyl-9H-fluorene-2-yl)-4,4,5,5-tetramethyl-[1,3,2]dioxaborolane] can be synthesized in a manner similar to that in Example 3-(1) except that Intermediate compound M15 is used instead of Intermediate compound M8 in Example 3-(1).

(3) Synthesis of Exemplified Compound E14

Exemplified compound E14 can be synthesized in a manner similar to that in Example 1-(4) except that Intermediate compound M15 is used instead of Intermediate compound M5 and Intermediate compound M16 is used instead of 2,7-bis(4,4,5,5-tetramethyl[1,3,2]dioxaborolane-2-yl)-9,9-dimethyl-9H-fluorene in Example 1-(4).

Example 10

Synthesis of Exemplified Compound E01

(1) Synthesis of Intermediate Compound M17

Intermediate compound M17 [2-bromo-3,9,9-trimethyl-9H-fluorene] can be synthesized in a manner similar to that in Example 2-(2) except that Intermediate compound M2 is used instead of Intermediate compound M6 and one-half equivalent of benziltrimethylammonium tribromide is used in Example 2-(2).

(2) Synthesis of Exemplified Compound E01

Exemplified compound E01 can be synthesized in a manner similar to that in Example 2-(3) except that Intermediate compound M17 is used instead of Intermediate compound M8 in Example 2-(3).

Example 11

Synthesis of Exemplified Compound A11

(1) Synthesis of Intermediate Compound M18

Intermediate compound M18 [2-(7-(9,9-dimethyl-9H-fluorene-2-yl)-3,6,9,9-tetramethyl-9H-fluorene-2-yl)-4,4,5,5-tetramethyl[1,3,2]dioxaborolane] can be synthesized in a manner similar to that in Example 3-(1) except that Intermediate compound M12 is used instead of Intermediate compound M8 in Example 3-(1).

(2) Synthesis of Exemplified Compound A11

Exemplified compound A11 can be synthesized in a manner similar to that in Example 1-(4) except that Intermediate compound M12 is used instead of Intermediate compound M5 and Intermediate compound M18 is used instead of 2,7-bis(4,4,5,5-tetramethyl[1,3,2]dioxaborolane-2-yl)-9,9-dimethyl-9H-fluorene in Example 1-(4).

Example 12

Synthesis of Exemplified Compound D11

Exemplified compound D11 can be synthesized in a manner similar to that in Example 1-(4) except that Intermediate compound M17 is used instead of Intermediate compound M5 and 3,6-bis(4,4,5,5-tetramethyl[1,3,2]dioxaborolane-2-yl)-9,9-dimethyl-9H-fluorene is used instead of 2,7-bis(4,4,5,5-tetramethyl[1,3,2]dioxaborolane-2-yl)-9,9-dimethyl-9H-fluorene in Example 1-(4).

Example 13

Measurement of $T_1$ of Exemplified Compounds C01 and D02

The first triplet excited state ($T_1$) levels of Exemplified compounds C01 and D02 measured with a fluorescence spectrophotometer (produced by Hitachi, Ltd.) in toluene at 77 K were 2.51 eV (494 nm) and 2.49 eV (497 nm), respectively. Therefore, the $T_1$ levels were high.

Comparative Example 1

The $T_1$ level of Comparative compound FL, as described below, measured by the same measuring method as that in Example 3 was 2.26 eV (548 nm).

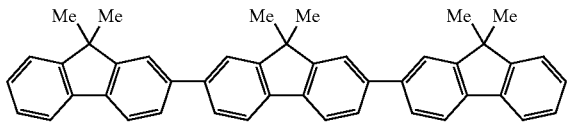

Comparative compound FL

Example 14

The organic light-emitting element having a structure shown in FIG. 3 was produced by the following method.

A film of indium tin oxide (ITO) serving as an anode 2 was formed on a glass substrate serving as a substrate 1 by a sputtering method so as to have a film thickness of 120 nm. The resulting substrate was used as a transparent electrically conductive support substrate. Films of the following organic layers and the electrode layer were formed on the ITO substrate continuously by vacuum deposition through resistance heating in a vacuum chamber at $10^{-4}$ Pa.

Hole transport layer 5 (40 nm): Compound J

Light-emitting layer 3 (30 nm): Exemplified compounds C01: Ir(ppy)$_3$ (weight ratio 15%) Electron transport layer 6 (35 nm): Bphen Anode 4 (1 nm+120 nm): KF+Al

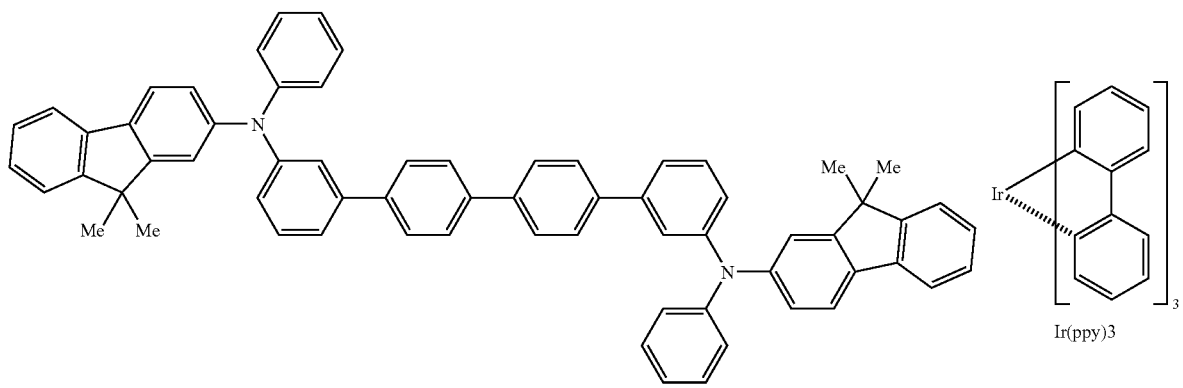
Compound J

Ir(ppy)3

The resulting organic EL element was covered with a protective glass plate in a dry air atmosphere and was sealed with an acrylic resin adhesive in such a way that deterioration of the element due to absorption of water did not occur.

When a direct current voltage of 5.9 V was applied to the thus produced element while the ITO electrode (anode 2) served as a positive electrode and the Al electrode (cathode 4) served as a negative electrode, emission of green light (CIE chromaticity: x=0.29, y=0.64) with a luminance of 2,400 cd/m² and a luminous efficacy of 57 cd/A was observed.

Example 15

An element was produced as in Example 14 except that Exemplified compound D02 was used instead of Exemplified compound C01. Emission of green light (CIE chromaticity: x=0.29, y=0.64) with a luminance of 2,400 cd/m² and a luminous efficacy of 41 cd/A was observed at an applied voltage of 5.5 V.

Comparative Example 2

An element was produced as in Example 12 except that CBP having the following structure was used instead of Exemplified compound C01.

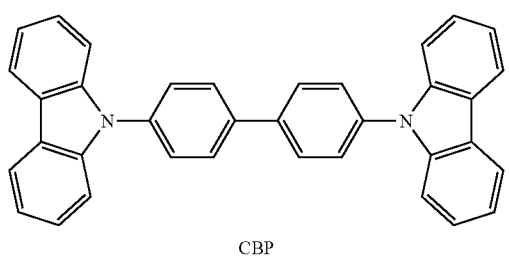
CBP

The evaluation of the element was conducted as in Example 14. When a voltage of 5.4 V was applied, emission of green light (CIE chromaticity: x=0.29, y=0.65) with a luminance of 2,400 cd/m² and a luminous efficacy of 34 cd/A was observed.

While the present invention has been described with reference to exemplary embodiments, it is to be understood that the invention is not limited to the disclosed exemplary embodiments. The scope of the following claims is to be accorded the broadest interpretation so as to encompass all modifications and equivalent structures and functions.

This application claims the benefit of Japanese Application No. 2007-039334 filed Feb. 20, 2007, which is hereby incorporated by reference herein in its entirety.

What is claimed is:

1. A material for an organic light-emitting element, the material being represented by General formula [II]:

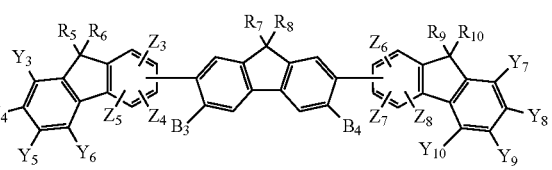

[II]

in the formula, $R_5$ to $R_{10}$ represent independently a hydrogen atom or a substituted or unsubstituted alkyl group, $Y_3$ to $Y_{10}$ represent independently a group selected from the group consisting of a hydrogen atom, an unsubstituted alkyl group, and an unsubstituted alkoxy group, $Z_3$ to $Z_8$ represent independently a group selected from the group consisting of a hydrogen atom, a substituted or unsubstituted alkyl group, and a substituted or unsubstituted alkoxy group, and $B_3$ and $B_4$ represent independently a group selected from the group consisting of a methyl group, an ethyl group, an isopropyl group, a t-butyl group, a cyclohexyl group, a trifluoromethyl group, and a methoxy group.

2. A material for an organic light-emitting element, the material being represented by General formula [III]:

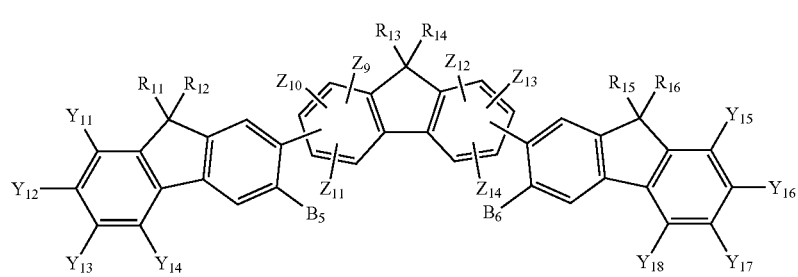

[III]

in the formula, $R_{11}$ to $R_{16}$ represent independently a hydrogen atom or a substituted or unsubstituted alkyl group, $Y_{11}$ to $Y_{18}$ represent independently a group selected from the group consisting of a hydrogen atom, an unsubstituted alkyl group, and an unsubstituted alkoxy group, $Z_9$ to $Z_{14}$ represent independently a group selected from the group consisting of a hydrogen atom, a substituted or unsubstituted alkyl group, and a substituted or unsubstituted alkoxy group, and $B_5$ and $B_6$ represent independently a group selected from the group consisting of a methyl group, an ethyl group, an isopropyl group, a t-butyl group, a cyclohexyl group, a trifluoromethyl group, and a methoxy group.

3. An organic light-emitting element comprising at least one pair of electrodes composed of an anode and a cathode, at least one of which is transparent or translucent, and an organic compound layer held between the pair of electrodes, wherein the organic compound layer contains the material for an organic light-emitting element according to claim 1.

4. The organic light-emitting element according to claim 3, wherein the organic compound layer comprises a light-emitting layer.

5. The organic light-emitting element according to claim 4, wherein the light-emitting layer comprises at least two compounds of a host compound and a guest compound, and the host compound comprises the material for an organic light-emitting element.

6. The organic light-emitting element according to claim 5, wherein at least one type of the guest compound comprises a phosphorescent compound.

7. The organic light-emitting element according to claim 3, wherein the organic light-emitting element comprises a field-emitting element for emitting light by applying a voltage between the pair of electrodes.

8. An organic light-emitting element comprising at least one pair of electrodes composed of an anode and a cathode, at least one of which is transparent or translucent, and an organic compound layer held between the pair of electrodes, wherein the organic compound layer contains the material for an organic light-emitting element according to claim 2.

9. The organic light-emitting element according to claim 8, wherein the organic compound layer comprises a light-emitting layer.

10. The organic light-emitting element according to claim 9, wherein the light-emitting layer comprises at least two compounds of a host compound and a guest compound, and the host compound comprises the material for an organic light-emitting element.

11. The organic light-emitting element according to claim 10, wherein at least one type of the guest compound comprises a phosphorescent compound.

12. The organic light-emitting element according to claim 8, wherein the organic light-emitting element comprises a field-emitting element for emitting light by applying a voltage between the pair of electrodes.

13. The organic light-emitting element according to claim 11, wherein the phosphorescent compound is an iridium complex having a phenyl isoquinoline as a ligand.

14. An apparatus having the organic light-emitting element according to claim 8, wherein the organic light-emitting element is set up on a substrate of the apparatus and the apparatus has a top emission configuration.

* * * * *